United States Patent [19]

Ishikawa et al.

[11] 4,399,134
[45] Aug. 16, 1983

[54] PYRROLOQUINOLINE AND BENZOQUINOLIZINE COMPOUNDS AND ANTIMICROBIAL COMPOSITIONS

[75] Inventors: Hiroshi Ishikawa; Testuyuki Uno; Masanobu Kano; Kazuyuki Nakagawa, all of Tokushima, Japan

[73] Assignee: Otsuka Pharmaceutical Co., Ltd., Tokyo, Japan

[21] Appl. No.: 320,027

[22] Filed: Nov. 10, 1981

[30] Foreign Application Priority Data

Nov. 10, 1980 [JP] Japan .............................. 55-158652
Apr. 24, 1981 [JP] Japan ................................ 56-63170

[51] Int. Cl.³ .................... A61K 31/47; C07D 455/02
[52] U.S. Cl. ............................. 424/246; 424/248.53; 424/250; 424/258; 544/58.2; 544/58.4; 544/58.6; 544/126; 544/361; 546/94
[58] Field of Search ................... 544/58.2, 58.4, 58.6, 544/126, 261; 546/94; 424/246, 248.53, 250, 258

[56] References Cited

U.S. PATENT DOCUMENTS 3,896,131  7/1975  Gerster ................................ 546/94
3,917,609  11/1975 Gerster ................................ 546/94
4,001,243  1/1977  Gerster ................................ 546/94

FOREIGN PATENT DOCUMENTS 55-40616  3/1980 Japan .
2020279  11/1979 United Kingdom .

Primary Examiner—Robert W. Ramsuer
Attorney, Agent, or Firm—Sughrue, Mion, Zinn, Macpeak and Seas

[57] ABSTRACT

A benzoheterocyclic compound of the formula (I)

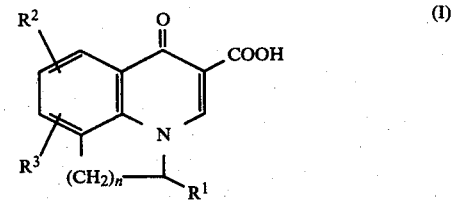

wherein $R^1$, $R^2$, $R^3$ and n are as defined, and its pharmaceutically acceptable salts, processes for preparing same and antibacterial composition containing the benzoheterocyclic compound as an active ingredient and a pharmaceutically acceptable carrier are disclosed.

23 Claims, No Drawings

PYRROLOQUINOLINE AND BENZOQUINOLIZINE COMPOUNDS AND ANTIMICROBIAL COMPOSITIONS

BACKGROUND OF THE INVENTION

1. Field of the Invention

This invention relates to certain benzoheterocyclic compounds and to pharmaceutically acceptable salts thereof which are useful as antimicrobial agents, processes for preparing the same, the pharmaceutical compositions containing the benzoheterocyclic compound or salts thereof.

2. Description of the Prior Art

It is known that certain types of polyheterocyclic compounds exhibit antimicrobial activities. For example, U.S. Pat. No. 3,917,609 to Gerster et al. discloses substituted derivatives of 1,2-dihydro-6-oxo-6H-pyrrolo-[3,2,1-ij]quinoline which are useful as antimicrobial agents or as intermediates for the preparation of antimicrobial agents.

Also, U.S. Pat. Nos. 3,896,131, 3,985,882, 3,969,463, 4,001,243 and 4,014,877 to Gerster et al. GB-A-2057440 and Japanese Patent Application (OPI) No. 30964/81 (the term "OPI" as used herein refers to a "published unexamined Japanese patent application") disclose 6,7-dihydro-1-oxo-1H,5H-benzo[ij]quinolizine derivatives having antimicrobial activities.

Further, GB-A-2020279 describes 6,7-dihydro-1-oxo-1H,5H-benzo[ij]quinolizine-2-carboxylic acid derivatives and 1,2-dihydro-6-oxo-6H-pyrrolo[3,2,1-ij]quinoline-5-carboxylic acid derivatives having antibacterial activities, and 1,2-dihydro-6-oxo-6H-pyrrolo[3,2,1-ij]quinoline-5-carboxylic-5-carboxylic acid derivatives having antibacterial activities.

However, the benzoheterocyclic compounds of the present invention are structurally different from such quinoline and quinolizine compounds.

SUMMARY OF THE INVENTION

One object of this invention is to provide benzoheterocyclic compounds having antimicrobial activity and low toxicity.

Another object of this invention is to provide an antimicrobial agent which is effective against bacteria which are resistant to conventional antibiotics such as penicillin, ampicillin, streptomycin, etc.

A further object of this invention is to provide a pharmaceutical composition containing the above antimicrobial agent or a pharmaceutically acceptable salt thereof in an antimicrobially effective amount.

Still a further object of this invention is to provide a process for preparing a benzoheterocyclic compound.

This invention provides a benzoheterocyclic compound represented by the formula (I)

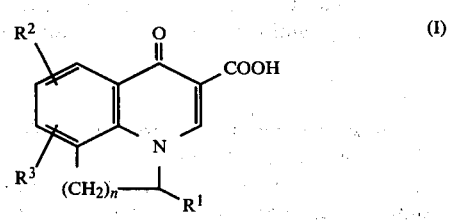

wherein $R^1$ represents a hydrogen atom or a lower alkyl group; $R^2$ represents a hydrogen atom or a halogen atom; $R^3$ represents a 1-pyrrolidinyl group which may be substituted with a hydroxymethyl group, a 1,2,5,6-tetrahydro-1-pyridyl group, a 1-piperazinyl group substituted with an oxo group or a lower haloalkyl group, or a group of the formula

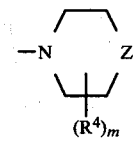

where $R^4$ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group or a carbamoyl group; Z represents an oxygen atom, a sulfur atom or a methylene group; m is 1 or 2; and n is an integer of 1 or 2; with the proviso that when n is 2, $R^3$ should not be a 1-piperazinyl group substituted with a lower haloalkyl group, and its pharmaceutically acceptable salts.

In another aspect, this invention provides a pharmaceutical composition containing a compound according to formula (I) or a pharmaceutically acceptable salt thereof in an antimicrobially effective amount.

Further, this invention provides processes for preparing the compounds of the formula (I) and pharmaceutically acceptable salts thereof.

DETAILED DESCRIPTION OF THE INVENTION

The term "lower alkyl" as used herein refers to a straight or branched chain alkyl group having from 1 to 6 carbon atoms, such as a methyl group, an ethyl group, a propyl group, an isopropyl group, a butyl group, a tert-butyl group, a pentyl group, a hexyl group and the like.

The term "halogen" as used herein includes a fluorine atom, a chlorine atom, a bromine atom and an iodine atom.

The term "phenyl-lower alkyl" as used herein refers to a phenylalkyl group having from 1 to 6 carbon atoms in the alkyl moiety. The alkyl moiety can be of straight chain or branched chain. Examples of the phenylalkyl group include a benzyl group, a 1-phenylethyl group, a 2-phenylethyl group, a 1-phenylpropyl group, a 2-phenylpropyl group, a 3-phenylpropyl group, a 1-phenylbutyl group, a 2-phenylbutyl group, a 3-phenylbutyl group, a 4-phenylbutyl group, a 1,1-dimethyl-2-phenylethyl group, a 5-phenylpentyl group, a 6-phenylhexyl group, a 2-methyl-3-phenylpropyl group and the like.

The term "lower alkanoyloxy" as used herein refers to a straight or branched chain alkanoyloxy groups having 1 to 6 carbon atoms such as a formyloxy group, an acetyloxy group, a propionyloxy group, a butyryloxy group, an isobutyryloxy group, a valeryloxy group, a hexanoyloxy group and the like.

The term "lower alkanoyl" as used herein refers to a straight or branched alkanoyl group having from 1 to 6 carbon atoms, such as a formyl group, an acetyl group, a propionyl group, a butyryl group, an isobutyryl group, a valeryl group, a hexanoyl group and the like.

The term "amino group which may be substituted with a lower alkyl group or a lower alkanoyl group" as used herein refers to an amino group which may be substituted with one or two straight or branched chain alkyl groups each having 1 to 6 carbon atoms or with a straight or branched chain alkanoyl group having 1 to 6 carbon atoms, such as an amino group, an N-methylamino group, an N-ethylamino group, an N-propylamino group, an N-isopropylamino group, an N-butylamino group, an N,N-dimethylamino group, an N,N-diethylamino group, an N-methyl-N-ethylamino group, an N,N-dipropylamino group, an N,N-diisopropylamino group, an N,N-dibutylamino group, an N-methyl-N-tert-butylamino group, a formylamino group, an acetylamino group, a propionylamino group, a butyrylamino group, an isobutyrylamino group, a valerylamino group, a hexanoylamino group, and the like.

The term "lower haloalkyl" as used herein refers to a straight or branched chain haloalkyl group having 1 to 6 carbon atoms, such as a trifluoromethyl group, a trichloromethyl group, a dichloromethyl group, a tribromomethyl group, a 2,2,2-trifluoroethyl group, a 2,2,2-trichloroethyl group, a 2-chloroethyl group, a 1,2-dichloroethyl group, a 3,3,3-trichloropropyl group, a 3-fluoropropyl group, a 4-chlorobutyl group, a 3-fluoropropyl group, a pentafluoroethyl group and the like.

The term "1-piperazinyl group substituted with an oxo group or a lower haloalkyl group" as used herein refers to a 1-piperazinyl group substituted with an oxo group or straight or branched chain haloalkyl group having 1 to 6 carbon atoms, such as a 3-oxo-1-piperazinyl group, a 4-trifluoromethyl-1-piperazinyl group, a 4-trichloromethyl-1-piperazinyl group, a 4-tribromomethyl-1-piperazinyl group, a 4-(2,2,2-trifluoroethyl)-1-piperazinyl group, a 4-(2,2,2-trichloroethyl)-1-piperazinyl group, a 4-(2,2,2-tribromoethyl)-1-piperazinyl group, a 4-(1,2-dichloroethyl)-1-piperazinyl group and the like.

Examples of "1-pyrrolidinyl group which may be substituted with a hydroxymethyl group" as used herein include a 1-pyrrolidinyl group, a 2-hydroxymethyl-1-pyrrolidinyl group and a 3-hydroxymethyl-1-pyrrolidinyl group.

Examples of the group represented by the formula

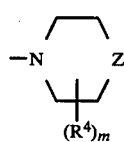

as used herein include a 1-piperidyl group, a 4-hydroxy-1-piperidyl group, a 3-hydroxy-1-piperidyl group, a 2-hydroxy-1-piperidyl group, a 3,4-dihydroxy-1-piperidyl group, a 2,3-dihydroxy-1-piperidyl group, a 3,5-dihydroxy-1-piperidyl group, a 4-methyl-1-piperidyl group, a 3,5-dimethyl-1-piperidyl group, a 2-methyl-1-piperidyl group, a 3-methyl-1-piperidyl group, a 4-butyl-1-piperidyl group, a 4-methoxy-1-piperidyl group, a 3-methoxy-1-piperidyl group, a 2-methoxy-1-piperidyl group, a 3,4-dimethoxy-1-piperidyl group, a 4-butoxy-1-piperidyl group, a 4-benzyl-1-piperidyl group, a 3-benzyl-1-piperidyl group, a 4-(4-phenylbutyl)-1-piperidyl group, a 4-carbamoyl-1-piperidyl group, a 2-carbamoyl-1-piperidyl group, a 3-carbamoyl-1-piperidyl group, a 4-acetyloxy-1-piperidyl group, a 3-acetyloxy-1-piperidyl group, a 2-acetyloxy-1-piperidyl group, a 4-butyryloxy-1-piperidyl group, a 4-N,N-dimethylamino-1-piperidyl group, a 2-N,N-dibutylamino-1-piperidyl group, a 4-acetylamino-1-piperidyl group, a 2-acetylamino-1-piperidyl group, a 3-acetylamino-1-piperidyl group, a 4-butyrylamino-1-piperidyl group, a 4-amino-1-piperidyl group, a 2-amino-1-piperidyl group, a 3-amino-1-piperidyl group, a 4-oxo-1-piperidyl group, a 2-oxo-1-piperidyl group, a 3-oxo-1-piperidyl group, a 3-hydroxymorpholino group, a morpholino group, a 3-hydroxythiomorpholino group, a thiomorpholino group, a 3-acetyloxymorpholino group, a 2-hydroxymorpholino group, a 3-methoxymorpholino group, and a 3-carbamoylmorpholino group. As for the groups represented by $R^1$ a lower alkyl group is preferred. Of the alkyl groups a methyl group and an ethyl group are preferred with a methyl group being most preferred.

As for the substituents represented by $R^2$ a halogen atom is preferred. Of the halogen atoms, chlorine and fluorine are preferred with fluorine being most preferred.

The position in the benzoheterocyclic ring to which the substituent represented by $R^2$ is attached is preferably the 8-position when n is 1 and the 9-position when n is 2, respectively.

On the other hand, the position in the benzoheterocyclic ring to which the substituent represented by $R^3$ is attached is preferably the 9-position when n is 1 and the 8-position when n is 2.

Preferably, n is 2.

Preferred examples of the subtituents represented by $R^3$ include a 1-piperidyl group, a morpholino group and a thiomorpholino group, each of which may be substituted with 1 or 2 of a hydroxy group and a lower alkanoyloxy group, with a 4-hydroxy-1-piperidyl group, a 3-hydroxy-1-piperidyl group, a 2-hydroxy-1-piperidyl group, a morpholino group, a thiomorpholino group and a 4-acetyloxy-1-piperidyl group being most preferred.

The compounds of this invention represented by the formula (I) can be prepared by various alternative procedures. For example, one procedure comprises reacting a benzoheterocyclic compound of the formula (II)

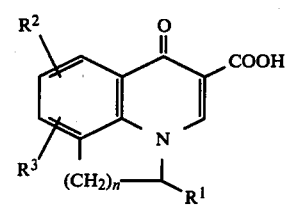

wherein $R^1$, $R^2$ and n have the same meaning as defined above, and $X^1$ represents a halogen atom, a lower alkanesulfonyloxy group or an arylsulfonyloxy group; with a compound represented by the formula (III)

$R^3H$      (III)

wherein $R^3$ has the same meaning as defined above.

The term "lower alkanesulfonyloxy" as used herein refers to a straight or branched alkanesulfonyloxy group having from 1 to 4 carbon atoms, such as a methanesulfonyloxy group, an ethanesulfonyloxy group, a propanesulfonyloxy group, an isopropanesulfonyloxy group, a butanesulfonyloxy group, a tert-butanesulfonyloxy group and the like.

The term "arylsulfonyloxy" as used herein includes a benzenesulfonyloxy group, a naphthalenesulfonyloxy group and the like. The aryl ring included in the arylsulfonyloxy group may be substituted with one or more of a halogen atom, a lower alkyl group, a hydroxy group, a nitro group and the like.

More particularly, the reaction of the compound of the formula (II) with the compound of the formula (III) the proportion of the compound of the formula (III) to the compound of the formula (II) is not particularly limited, and can be varied broadly. Usually the reaction can be carried out using at least an equimolar amount, and preferably from 1 to 6 mols, of the compound of the formula (III) per mole of the compound of the formula (II).

The reaction can be carried out in an inert solvent. Examples of suitable inert solvent include water, lower alcohols such as methanol, ethanol, isopropanol, butanol, amyl alcohol, isoamyl alcohol, etc., aromatic hydrocarbons such as benzene, toluene, xylene, etc., ethers such as tetrahydrofuran, dioxane, diglyme (diethylene glycol dimethyl ether), etc., dimethyl sulfoxide, dimethylformamide, hexamethylphosphoric triamide and the like, with dimethyl sulfoxide, dimethylformamide and hexamethylphosphoric triamide being preferred.

The above reaction may be conducted in the presence of an acid acceptor in an amount of at least an approximately equimolar amount, and preferably from 1 to 2 mols, of the acid acceptor per mol of the compound of the formula (II). Examples of suitable acid acceptor include alkali metal hydroxides such as sodium hydroxide, potassium hydroxide, etc., inorganic carbonates such as sodium carbonate, potassium carbonate, potassium hydrogen carbonate, sodium hydrogen carbonate, etc., tertiary amines such as pyridine, quinoline, N-methylpyrrolidone, triethylamine, etc.

The above reaction can be carried out in an inert solvent, desirably under pressurized conditions, i.e., at a pressure of from about 1 to 20 atms (atmospheres), and preferably from 1 to 10 atms, at a temperature of from about 100° to 250° C., and preferably from 140° to 200° C., for a period of about 5 to about 20 hours, thus preparing the compounds of this invention represented by the formula (I).

The benzoheterocyclic compounds of the formula (II) which can be used as the starting material for preparing the compounds of this invention represented by the formula (I) are known compounds, as described in U.S. Pat. Nos. 3,917,609, 3,896,131, 3,985,882, 3,969,463, 4,001,243 and 4,014,877.

On the other hand, the compounds of the formula (III), another starting material of the compounds of this invention represented by the formula (I), are known and commercially available.

Of the compounds represented by the formula (I), those in which $R^4$ represents a lower alkanoyloxy group or an amino group substituted with a lower alkanoyl group can be prepared by acylating a corresponding compound of the formula (I) in which $R^4$ represents a hydroxy group or an amino group with an acylating agent.

Examples of suitable acylating agent include lower alkanoic acids such as acetic acid, propionic acid, butyric acid, isobutyric acid, etc., the acid anhydrides thereof such as acetic anhydride or the acid halides thereof such as acetyl chloride, propionyl bromide, butyryl bromide, isobutyryl bromide, etc. When using lower alkanoic acid anhydrides and acid halides as an acylating agent, the acylation reaction is carried out in the presence of a basic compound.

Examples of useful basic compounds include, for example, alkali metals such as sodium, potassium and the like, hydroxides, carbonates and bicarbonates thereof such as sodium hydroxide, potassium hydroxide, sodium carbonate, potassium carbonate, sodium hydrogen carbonate and the like, aromatic amines such as pyridine, piperidine and the like. Of these, potassium carbonate is preferred.

The above reaction can proceed either in the absence of solvents or in the presence of a solvent. Usually, the reaction is carried out in the presence of a suitable solvent. Examples of suitable solvent which can be used include ketones such as acetone, methyl ethyl ketone and the like, ethers such as diethyl ether, dioxane and the like, aromatic hydrocarbons such as benzene, toluene, xylene and the like, and water. Of these, acetone and water are preferred.

A suitable amount of the acylating agent is an equimolar amount to a large excess amount, usually 5 to 10 mols per mol of the starting compound.

The reaction can be carried out at a temperature of about 0° to about 150° C., preferably 0° to 80° C., and completed usually in about 1 to about 20 hours. When lower alkanoic acids are used as an acylating agent the acylation reaction can be carried out advantageously in adding a mineral acid such as sulfuric acid, hydrochloric acid and the like or a sulfonic acid such as p-toluenesulfonic acid, benzenesulfonic acid, ethanesulfonic acid and the like as a dehydrating agent in the reaction system and maintaining the reaction temperature preferably at 50° to 120° C.

Of the compounds of the formula (I), those in which $R^4$ represents a hydroxy group or an amino group can also be prepared by hydrolyzing a corresponding compound of the formula (I) in which $R^4$ represents a lower alkanoyloxy group or an amino group substituted with a lower alkanoyl group.

The hydrolysis can be carried out in a suitable solvent in the presence of an acid or a basic compound. Examples of suitable solvents include water, lower alcohols such as methanol, ethanol, isopropanol and the like, ethers such as dioxane, tetrahydrofuran and the like and mixtures thereof. As the acid can be used mineral acids such as hydrocloric acid, sulfuric acid, hydrobromic acid and the like. As the basic compound can be used metal hydroxides such as sodium hydroxide, potassium hydroxide, calcium hydroxide and the like.

The above reaction can proceed usually at room temperature to 150° C., preferably 80° to 120° C. and be completed generally in about 1 to 15 hours.

Of the compounds of this invention, those in which $R^3$ represents a 1-piperazinyl group substituted with a haloalkyl group can be prepared by preparing a compound of the formula (IV)

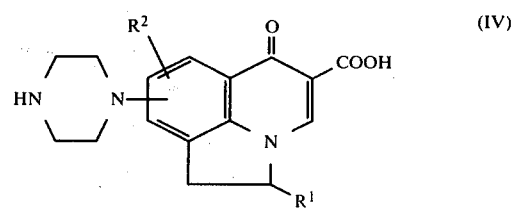

wherein $R^1$ and $R^2$ have the same meanings as defined above, according to the process described above and then reacting the compound of the formula (IV) with a lower haloalkane. In the above reaction, conventional dehydrohalogenation reaction can be used. More particularly, the above reaction can be carried out in a solvent such as water, lower alcohols such as methanol, ethanol, isopropanol and the like, ketones such as acetone, methyl ethyl ketone and the like, ethers such as diethyl ether, dioxane and the like, and aromatic hydrocarbons such as benzene, toluene, xylene and the like in the presence of a suitable dehydrohalogenating agent such as sodium hydroxide, potassium hydroxide, potassium carbonate, sodium carbonate, sodium metal, potassium metal, pyridine, piperidine and the like. The amount of the lower haloalkane to be used is 1 mol to excess amount, preferably 1 to 3 mols, per mol of the compound of the formula (IV). The reaction can proceed at room temperature to 150° C., preferably 50° to 120° C. and be completed generally in about 1 to 12 hours.

The compounds of the formula (I) of this invention can also be prepared according to Reaction Scheme-1 below.

In the above formulae, $R^1$, $R^2$, $R^3$ and n have the same meanings as defined above, and $R^6$, $R^7$, $R^8$, $R^9$ and $R^{10}$ each represents a lower alkyl group.

The reaction between the compound of the formula (V) and the compound of the formula (VI) can be carried out in the absence of solvents or in a suitable solvent. Examples of suitable solvent include alcohols such as methanol, ethanol, isopropanol and the like, aromatic hydrocarbons such as benzene, toluene and the like, acetonitrile, dimethylformamide, dimethyl sulfoxide, hexamethylphosphoric triamide and the like. It is preferred that the reaction be carried out in the absence of solvents. The amount of the compound of the formula (VI) to be used is usually at least 1 mol, preferably 1 to 1.5 mols, per mol of the compound of the formula (V). The reaction temperature is usually room temperature to about 150° C., preferably 60° to 120° C., and the reaction can be completed usually in about 0.5 to 6 hours, thus readily forming the compound of the formula (VIII).

The reaction between the compound of the formula (V) and the compound of the formula (VII) can be carried out in an analogous manner to that between the compounds of the formula (V) and the compound of the

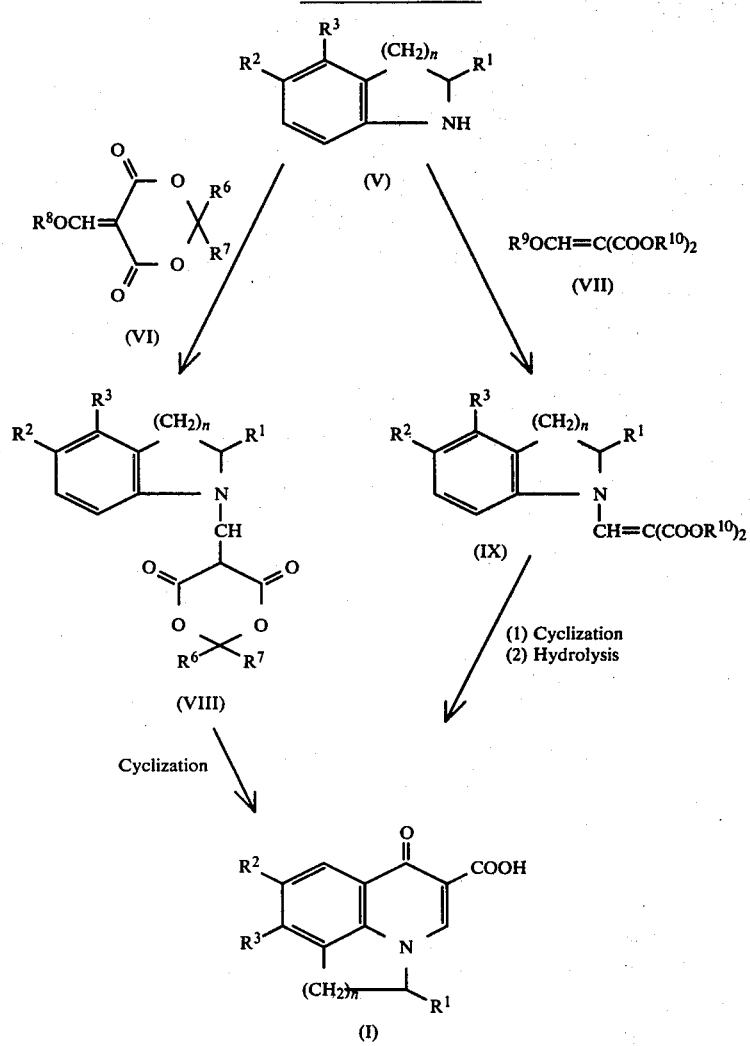

formula (VI), thus readily forming the compound of the formula (IX).

Cyclization reaction of the compound of the formula (VIII) or (IX) can be carried out using various conventional cyclization reactions such as cyclization by heating, cyclization with an acidic substance such as phosphorus oxychloride, phosphorus pentachloride, phosphorus trichloride, thionyl chloride, concentrated sulfuric acid, polyphosphoric acid and the like. When cyclization is effected by heating the reaction can proceed in a solvent such as hydrocarbons and ethers both having a high boiling point, e.g., tetralin, diphenyl ether, diethylene glycol dimethyl ether and the like at a temperature of, usually, 100° to 250° C., preferably 150° to 200° C. When cyclization is effected with an acidic substance the reaction can be carried out in the presence of 1 mol to excessive amount, preferably 10 to 20 mols, of the acidic substance per mol of the compound of the formula (VIII) or (IX) at a temperature of usually 100° to 150° C. for about 0.5 to 6 hours.

When a compound of the formula (II) is used as a starting compound objective compound of the formula (I) can be obtained according to the above cyclization reaction.

Further, when a compound of the formula (IX) is used as a starting compound, a compound of the formula (X)

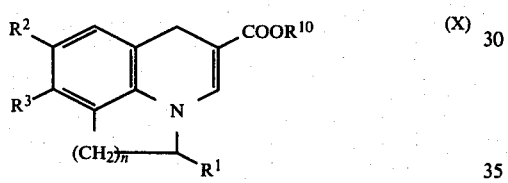

wherein $R^2$, $R^3$, $R^{10}$ and n have the same meanings as defined above, can be obtained according to the above cyclization reaction, and the compound of the formula (X) can be subjected, with or without isolation, to the subsequent hydrolysis reaction.

The hydrolysis reaction of the compound of the formula (X) can be carried out by conventional methods, for example, in the presence of a conventional catalyst such as a basic compound, e.g., sodium hydroxide, potassium hydroxide, barium hydroxide and the like, a mineral acid, e.g., sulfuric acid, hydrochloric acid, nitric acid, or an organic acid, e.g., acetic acid, aromatic sulfonic acid and the like.

The reaction can be carried out generally in a conventional solvent such as water, methanol, ethanol, isopropanol, dioxane, ethylene glycol, acetone, methyl ethyl ketone, acetic acid and the like. The reaction temperature is usually room temperature to 200° C., preferably 50° to 150° C. Thus, the compound of the formula (I) can be prepared.

The compounds of the formula (V) used in this invention are novel compounds and can be prepared according to Reaction Schemes-2, -3, -4 and -5 below.

Reaction Scheme-2

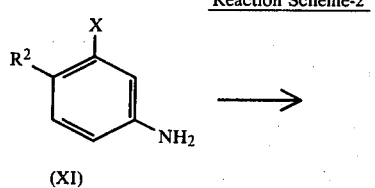

(XI)

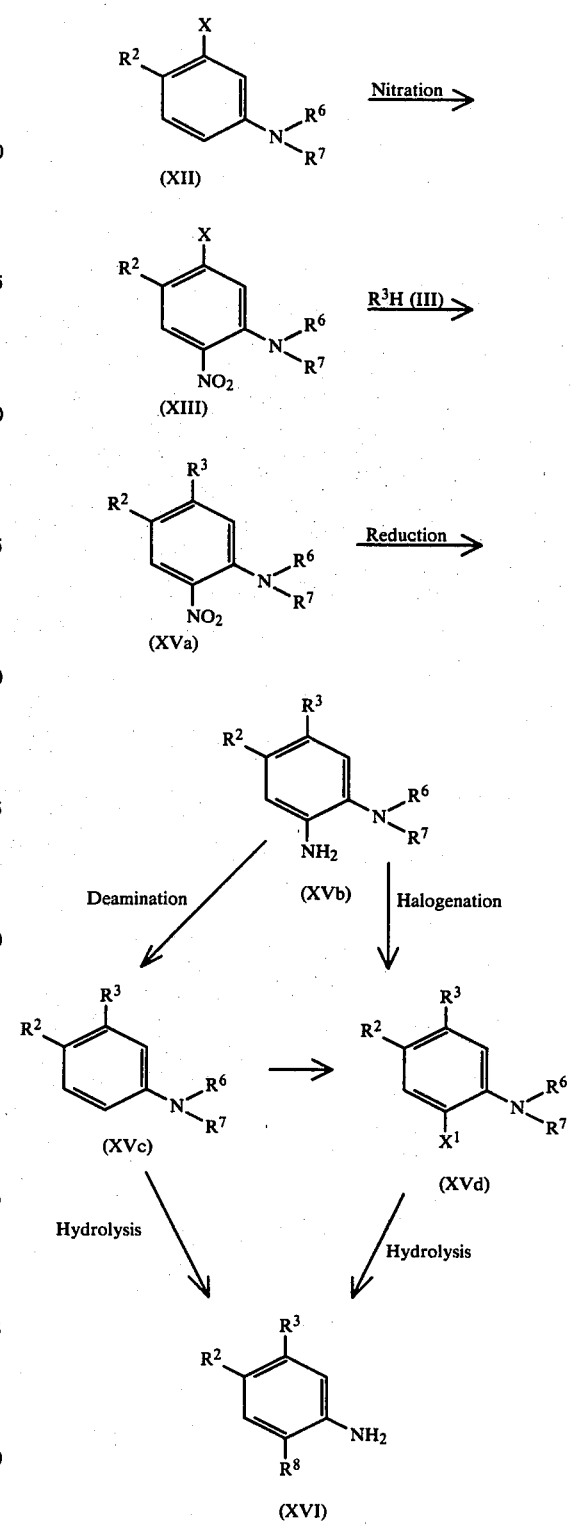

In the above formulae, $R^6$ represents a hydrogen atom, $R^7$ represents a lower alkanoyl group, or $R^6$ and $R^7$, together with the nitrogen atom to which they are attached, can form a group of the formula

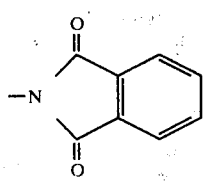

$R^8$ represents a hydrogen atom or a halogen atom, X and $X^1$ each represents a halogen atom; and $R^2$ and $R^3$ have the same meanings as defined above.

In the above Reaction Scheme-2, the reaction of converting an aniline derivative of the formula (XI) to an aniline derivative of the formula (XII) can be carried out by reacting the compound of the formula (XI) with an acid anhydride or acid halide in a solvent. Examples of suitable solvent which can be used include lower alcohols such as methanol, ethanol, isopropanol and the like, ethers such as dioxane, THF and the like, acetic acid, pyridine, dimethylformamide, dimethyl sulfoxide, hexamethylphosphoric triamide and the like. As the acid anhydride can be used, for example, acetic anhydride, phthalic anhydride and the like and as the acid halide can be used, for example, acetyl chloride, propionyl chloride, butyryl bromide and the like. The amount of the acid anhydride or acid halide to be used is at least about 1 mol, preferably 1 to 3 mols, per mol of the aniline derivative (XI). The reaction can be carried out at a temperature of usually room temperature to about 200° C., preferably room temperature to 160° C. and completed generally in 0.5 to 5 hours.

Nitration of the compound of the formula (XII) can be carried out using any conventional nitration agent, for example, fuming sulfuric acid, concentrated nitric acid, mixed acids (a mixture of nitric acid with sulfuric acid, fuming sulfuric acid, phosphoric acid or acetic anhydride), a combination of an alkali metal nitrate such as potassium nitrate, sodium nitrate and the like and sulfuric acid. The amount of the nitration agent to be used is usually at least about 1 mol, preferably 1 to 1.5 mols, per mol of the compound of the formula (XII). The reaction can be carried out at a temperature of usually $-20°$ to 50° C., preferably $-10°$ C. to room temperature and completed generally in about 1 to 7 hours.

The reaction between the compound of the formula (XIII) and the compound of the formula (III) can be carried out in the presence of a solvent. Examples of suitable solvent include aromatic hydrocarbons such as benzene, toluene, xylene and the like, lower alcohols such as methanol, ethanol, isopropanol and the like, ethers such as dioxane, tetrahydrofuran, ethylene glycol dimethyl ether, diethyl ether and the like, polar solvents such as N-methylpyrrolidone, DMF, DMSO, hexamethylphosphoric triamide and the like. The above reaction can proceed more advantageously in the presence of a basic compound as an acid acceptor. Examples of suitable basic compound include sodium carbonate, sodium hydroxide, sodium hydrogencarbonate, sodium amide, sodium hydride, tertiary amines such as triethylamine, tripropylamine and the like, pyridine, quinoline, etc. The amount of the compound of the formula (III) to be used is usually 1 to 10 mols, preferably 3 to 7 mols per mol of the compound (XIII). The reaction can be carried out at a temperature of usually 50° to 150° C., preferably 50° to 100° C. and completed generally in about 1.5 to 10 hours.

In the reduction of the compounds of the formula (XVa) reduction reaction of nitro groups conventionally used can be used. For example, (1) a process in which reduction is carried out catalytically in a solvent such as water, methanol, ethanol, isopropanol, THF, diethyl ether and the like using platinum oxide, palladium black, palladium on carbon or the like as a reduction catalyst in an atmosphere of hydrogen gas at a pressure of usually 1 to 10 atms, preferably 1 to 3 atms, at a temperature of generally $-30°$ C. to the boiling point of the solvent used, preferably about 0° C. to room temperature, (2) a process in which reduction is carried out in an anhydrous solvent such as diethyl ether, THF and the like using lithium aluminum hydride as a reducing agent, or (3) a process in which reduction is carried out in a solvent such as water, ethanol, methanol, acetic acid and the like using a metal compound such as iron, zinc, tin, stannous chloride and an acid such as hydrochloric acid, acetic acid and the like, can be used. Of the above processes, process (3) is preferred.

The reaction can be carried out at a temperature of usually 0° to 100° C., preferably 10° to 50° C. and completed generally in about 10 minutes to 3 hours. The amount of the metal compound to be used is usually at least about 1 mol, preferably 2 to 5 mols, per mol of the compound of the formula (XVa).

Deamination reaction of the compound of the formula (XVb) can be carried out in a solvent such as water and the like by converting the compound of the formula (XVb) to a corresponding diazonium salt using an acid such as sulfuric acid, hydrochloric acid, hydrobromic acid, fluoroboric acid and the like and sodium nitrite and then reacting the diazonium salt with a hydrogenation agent such as alcohols, e.g., ethanol, etc., aldehydes, e.g., alkaline formaldehyde, etc., metals, e.g., zinc, copper, etc., or hypophosphorous acid, etc. The amount of sodium nitrite to be used is usually 1 to 2 mols, preferably 1 to 1.5 mols, per mol of the compound of the formula (XVb). On the other hand, the amount of the hydrogenation agent to be used is usually large excess amount, preferably 5 to 15 mols per mol of the compound of the formula (XVb). The reaction can be carried out at a temperature of usually $-20°$ C. to room temperature, preferably $-5°$ to 5° C. and completed generally in about 5 to 24 hours.

The halogenation reaction of the compound of the formula (XVb) can be carried out by converting the compound of the formula (XVb) to a corresponding diazonium salt in a solvent such as water using an acid such as sulfuric acid, hydrochloric acid, hydrobromic acid, fluoroboric acid and the like and sodium nitrite and then, either reacting the resulting diazonium salt with copper powder or a copper halide (e.g., cuprous bromide, cuprous chloride, cupric chloride, etc.) in the presence of a hydrohalogenic acid (e.g., hydrobromic acid, hydrochloric acid, etc.), or reacting the diazonium salt with potassium iodide in the presence or absence of copper powder. It is preferred that the reaction be carried out by reacting the compound of the formula (XVb) with copper powder in the presence of a hydrohalogenic acid.

The amount of sodium nitrite to be used is usually 1 to 2 mols, preferably 1 to 1.5 mols, per mol of the compound of the formula (XVb). On the other hand, the amount of the copper powder to be used is usually 1 to 3 mols, preferably 1 to 2 mols, per mol of the compound (XVb). The reaction can be carried out at a temperature of usually $-20°$ C. to about room temperature, preferably −5° to 5° C. and completed generally in about 10 minutes to 5 hours.

Further, the compound of the formula (XVd) can also be prepared by reacting the compound of the formula (XVc) with a halide such as chloride, bromide, etc.

The reaction between the compound of the formula (XVc) and a halide can be carried out in a solvent, for example, a halogenated hydrocarbon such as dichloromethane, chloroform, carbon tetrachloride, etc., acetic acid, concentrated sulfuric acid and the like in the presence of a Lewis acid such as aluminum chloride, zinc chloride, iron chloride, tin chloride, boron tribromide, boron trifluoride, concentrated sulfuric acid, etc., or a catalyst such as silver sulfate, iodine, etc., at about room temperature to 100° C. for about 0.5 to 5 hours. The amount of the halide to be used is usually at least 1 mol, preferably 1 to 3 mols, of the halide per mol of the compound of the formula (XVc). On the other hand, the amount of the catalyst to be used is usually at least 1 mol, preferably 1 to 3 mols, of the catalyst per mol of the compound of the formula (XVc).

The hydrolysis reaction of the compounds of the formula (XVc) or (XVd) can be carried out in a suitable solvent in the presence of a basic compound. Examples of suitable solvent which can be used include water, methanol, ethanol, isopropanol and the like. Examples of suitable basic compound include potassium hydroxide, sodium hydroxide, potassium carbonate, sodium carbonate, sodium hydrogencarbonate and the like. The amount of the basic compound to be used is usually large excessive amount, preferably 4 to 8 mols per mol of the compound of the formula (XVc) or (XVd). The reaction can be carried out at a temperature of usually about room temperature to 150° C., preferably 50° to 100° C. and completed generally in about 10 minutes to 5 hours.

acids such as sulfuric acid and the like, phosphorus compounds such as phosphorus oxychloride, phosphorus pentachloride, phosphorus trichloride and the like. The amount of such condensing agent is usually a large excessive amount relative to the amount of the compound of the formula (XVIa). The proportion of the compound of the formula (XVII) to the compound of the formula (XVIa) is usually at least about 1 mol, preferably 1 to 1.5 mols, of the former per mol of the latter. The reaction can be carried out at a temperature of usually 70° to 150° C. and completed generally in several minutes to about 1 hour.

In the reduction reaction of the compound of the formula (XVIII) conventional catalytic reduction can be used. Examples of the reduction catalyst which can be used in the reaction include platinum oxide, platinum-carbon, palladium black, palladium-carbon, Raney nickel and the like. Examples of solvent which can be used include water, lower alcohols such as methanol, ethanol, isopropanol and the like, ethers such as THF, diethyl ether and the like, acetic acid, acetic anhydride, etc. The reaction can be carried out in an atmosphere of hydrogen gas at a pressure of usually 1 to 10 atms, preferably 2 to 5 atms at a temperature of generally −30° C. to the boiling point of the solvent used, preferably about 0° C. to room temperature. The amount of the reduction catalyst is usually 5 to 15% by weight, preferably 5 to 10% by weight based on the weight of the compound of the formula (XVIII).

Reaction Scheme-3

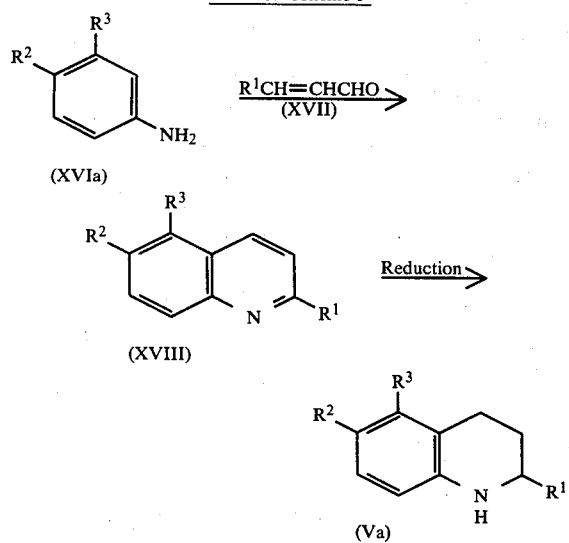

In the above formulae, $R^1$, $R^2$ and $R^3$ have the same meanings as defined above.

The reaction between the compound of the formula (XVIa) and the compound of the formula (XVII) can be carried out in the presence of a condensing agent without a solvent. Examples of the condensing agent which can be used include phosphoric acids such as phosphorus pentoxide, polyphosphoric acid and the like, mineral Reaction Scheme-4

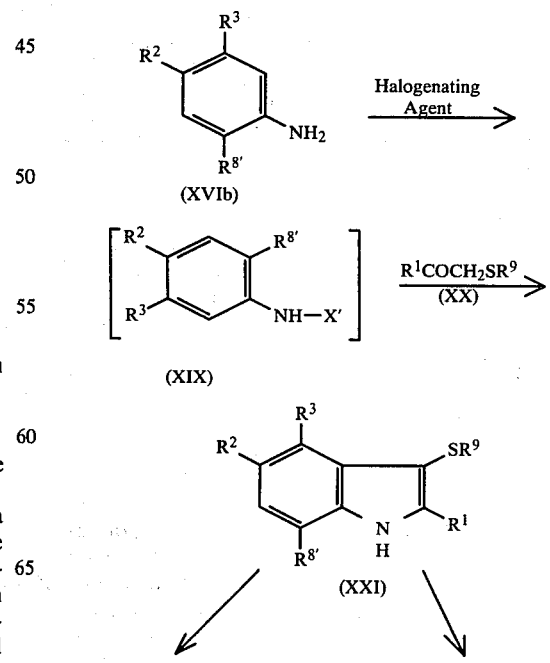

-continued
Reaction Scheme-4

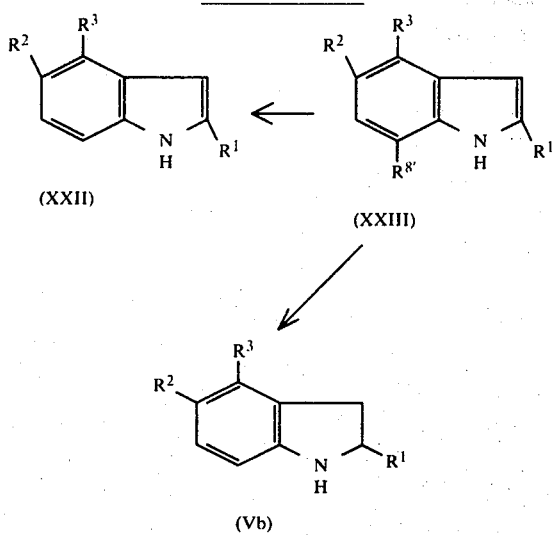

In the above formulae, $R^1$, $R^2$ and $R^3$ have the same meanings as defined above, $R^{8'}$ and $X'$ each represents a halogen atom, and $R^9$ represents a lower alkyl group.

The reaction between the aniline derivative of the formula (XVIb) and a halogenating agent can be carried out in a suitable solvent. Any conventional solvents that give no adverse effect on the reaction can be used. Example of suitable solvent include halogenated hydrocarbons such as chloroform, methylene chloride and the like, ethers such as dioxane, diethyl ether, tetrahydrofuran, aromatic hydrocarbons such as benzene, toluene, xylene and the like, lower alcohols such as methanol, ethanol, isopropanol and the like, polar solvents such as dimethyl sulfoxide, hexamethylphosphoric triamide, acetonitrile and the like. As the halogenating agent can be used various compounds which can be used in conventional halogenation reaction. Representative examples thereof include N-bromosuccinimide, N-chlorosuccinimide, sodium hypobromite, sodium hypochlorite, bleaching powder, thionyl chloride, tertbutyl hypochlorite and the like. The amount of the halogenating agent to be used is usually at least 1 mol, preferably 1 to 1.5 mols, per mol of the starting compound. The reaction can be carried out at a temperature of generally −78° to 0° C., preferably −60° to −10° C. and can be completed usually in several minutes.

Thus, an intermediate compound of the formula (XIX) can be obtained. The compound of the formula (XIX) can be isolated from the reaction system and subjected to subsequent reaction steps. Alternatively, it can be subjected to subsequent reaction with the thio compound of the formula (XX) without isolation from the reaction system.

The reaction between the intermediate compound of the formula (XIX) and the thio compound of the formula (XX) can be carried out usually in the presence of a basic compound in the same solvent as described above under the same temperature conditions as described above. Examples of suitable basic compound which can be used include inorganic basic compounds such as potassium carbonate, sodium carbonate, sodium hydroxide, sodium hydrogencarbonate, sodium amide, sodium hydride and the like and inorganic basic compounds such as tertiary amines, e.g., triethylamine, tripropylamine, pyridine, quinoline and the like. The proportion of the compound of the formula (XIX) to the compound of the formula (XX) is generally at least 1 mol, preferably 1 to 1.5 mols, of the former per mol of the latter. The reaction can be completed usually in about 1 to 5 hours. Thus, the indole derivative of the formula (XXI) of this invention can be obtained.

The desulfurization reaction of the compound of the formula (XXI) can be carried out in a solvent in the presence of a suitable catalyst. Examples of suitable catalyst include aluminum amalgam, lithiumlower alkylamine, Raney nickel, Raney cobalt, triethyl phosphite, triphenylphosphine and the like, with Raney nickel being preferred. Examples of the solvent include alcohols such as methanol, ethanol, isopropanol and the like, ethers such as dioxane, THF, diethyl ether and the like. The reaction can be carried out at a temperature of about 0° to 200° C., preferably about room temperature and completed in about 1 to 5 hours. The amount of the catalyst to be used is usually about 1 to 10 parts by weight per part by weight of the indole derivative of the formula (XXI).

The dehalogenation reaction of the compound of the formula (XXIII) thus obtained can be carried out in a manner analogous to conventional dehalogenation. For example, a process in which zinc powder is used in acetic acid or catalytic reduction process can be used. The former process can be carried out usually at a temperature of about 50° to 150° C. for about 2 to 5 hours. The amount of the zinc powder to be used is usually about 2 to 5 mols per mol of the compound of the formula (XXIII). On the other hand, the catalytic reduction process can advantageously be carried out in a suitable solvent such as alcohols, e.g., methanol, ethanol, isopropanol and the like, ethers, e.g., diethyl ether, dioxane, tetrahydrofuran and the like, acetic acid, etc., using a catalyst such as palladium-carbon, palladium black and the like. The reaction can be carried out at a temperature of about 0° C. to room temperature under a pressure of about 1 to 3 atms for about 0.5 to 3 hours. The amount of the catalyst to be used is as that used conventionally, for example, about 1/10 to 1/20 part by weight per part by weight of the compound of the formula (XXIII). It is also possible to add sodium acetylate and the like during the above catalytic reduction.

Further, the compound of the formula (XXII) can also be prepared directly from the indole derivative of the formula (XXI). This reaction can be carried out usually in a suitable solvent using a catalyst. Any solvents that are exemplified for the above desulfurization reaction can be used. As the catalyst can be used triethyl phosphite, triphenylphosphine, Raney nickel and the like, with Raney nickel being preferred. The reaction temperature is usually 0° to 200° C., preferably 50° to 100° C. Other conditions are the same as the above desulfurization reaction.

The reduction of the compound of the formula (XXII) thus obtained can be carried out catalytically in a suitable inert solvent. Examples of suitable inert solvent include alcohols such as methanol, ethanol, isopropanol and the like, ethers such as dioxane, tetrahydrofuran, diethyl ether and the like, acetic acid, water, etc. Examples of reduction catalyst include platinum, Raney nickel, palladium black, copper chromate, platinum-carbon, palladium-carbon, radium-carbon, ruthenium-carbon and the like. The reduction reaction can advantageously be carried out at 0° to 200° C. under a pressure of 1 to 250 atms for about 0.5 to 10 hours. The amount of the catalyst is usually about 1/10 to 1/20 part by weight per part by weight of the compound of the formula (XXII).

(XVb). The reduction of the compound of the formula (XXVIII) can be carried out in a manner analogous to that of the quinoline derivative of the formula (XVIII).

Reaction Scheme-5

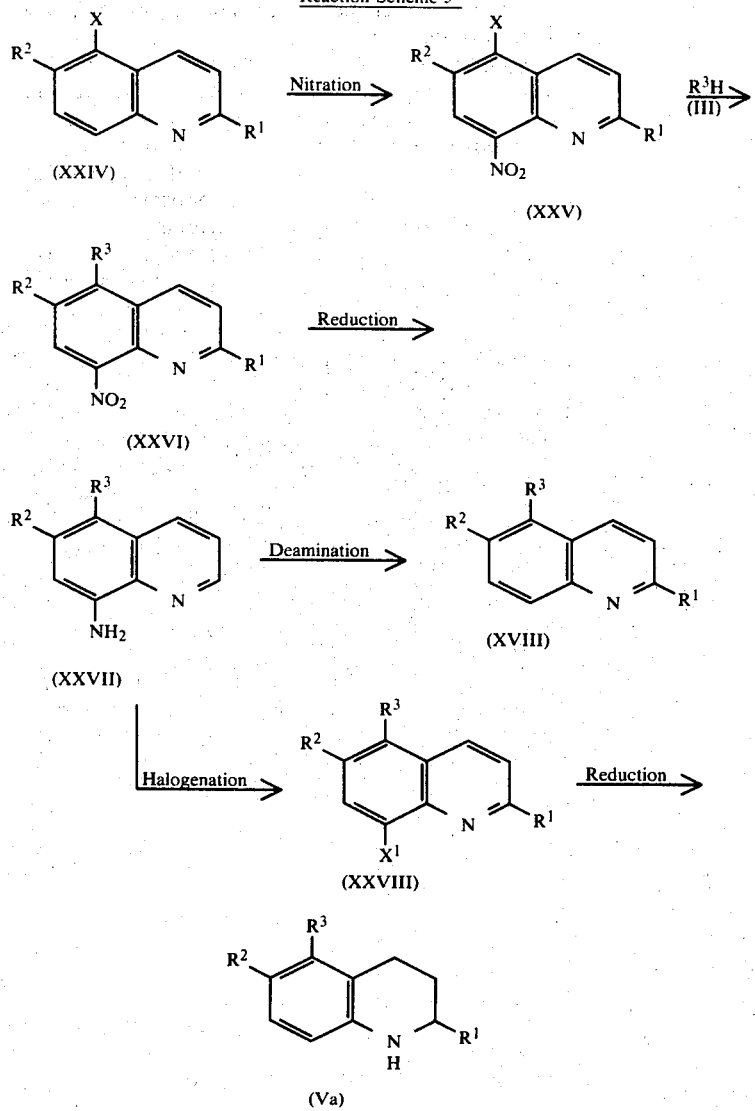

In the above formaule, X, X$^1$, R$^1$, R$^2$ and R$^3$ have the same meanings as defined above.

The nitration reaction of the quinoline derivative of the formula (XXIV) can be carried out in a manner analogous to the nitration reaction of the aniline derivative of the formula (XII). The reaction between the quinoline derivative of the formula (XXV) and the compound of the formula (III) can be carried out in a manner analogous to the reaction between the aniline derivative of the formula (XIII) and the compound of the formula (III). The reduction of the nitro group of the compound of the formula (XXVI) can be carried out in a manner analogous to the reduction of the nitro group of the compound of the formula (XVa). The deamination reaction of the quinoline derivative of the formula (XXVII) can be carried out in a manner analogous to the deamination of the compound of the formula (XVb). The halogenation reaction of the quinoline derivative of the formula (XXVII) can be carried out in a manner analogous to that of the aniline derivative of the formula Further, the compound of the formula (I) can be prepared in Reaction Scheme-6 below.

Reaction Scheme-6

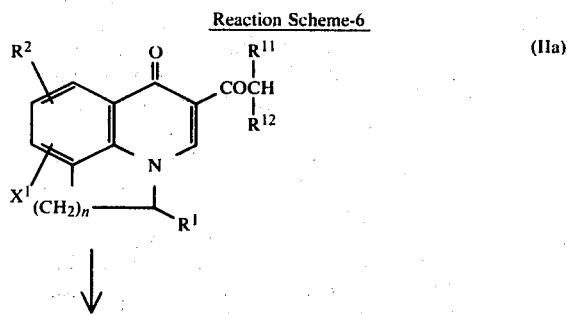

-continued
Reaction Scheme-6

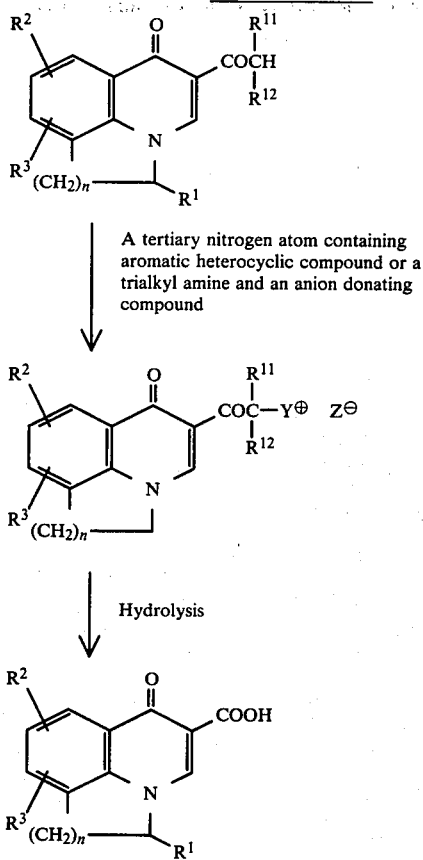

In the above formulae, $R^1$, $R^2$, $R^3$, $X^1$ and n have the same meanings as defined above, $R^{11}$ and $R^{12}$ each represents a hydrogen atom or a lower alkyl group, Y represents an aromatic heterocyclic ring containing a tertiary nitrogen atom through which it is connected or a trialkylamino group, and Z represents an anionic ion.

The compound of the formula (IIa) which can be used in the above reaction as a starting compound is a known compound.

The reaction between the compound of the formula (IIa) and the compound of the formula (III) can be carried out under conditions analogous to those used in the reaction between the compound of the formula (II) and the pyrrolidine which may be substituted with a hydroxymethyl group, a 1,2,5,6-tetrahydropyridine, a piperazine substituted with an oxo group or a lower haloalkyl group or the compound of the formula (III).

The preparation of the compounds of the formula (I) from the compound of the formula (a) can be effected by reacting the compound of the formula (Ia) with a tertiary nitrogen atom containing aromatic heterocyclic compound or a trialkylamine and an anion donating compound in an appropriate inert solvent to obtain a compound of the formula (Ib) and hydrolyzing the compound of the formula (Ib) thus obtained after isolation or without isolation thereof to obtain the compound of the formula (I).

In the above reaction, examples of suitable tertiary nitrogen atom containing aromatic heterocyclic compound include unsubstituted pyridine and alkyl substituted pyridine compounds such as picolines, lutidines, etc., quinoline and alkyl substituted quinolines such as quinaldine, lepidine, etc.

Examples of suitable trialkylamine include trialkylamines having 1 to 6 carbon atoms in each alkyl moiety, such as trimethylamine, triethylamine, tripropylamine, triisopropylamine, etc.

Examples of suitable anion donating compound include those compounds which can donate a halogen ion such as an iodine ion, a bromine ion, a chlorine ion, etc., for example, iodine, bromine, chlorine, or those compounds which can donate a sulfate residue, a phosphate residue, a perchlorate residue, etc., for example, sulfuric acid, phosphoric acid, perchloric acid, etc.

Examples of suitable inert solvent which can be used in the above reaction include lower alcohols such as methanol, ethanol, isopropanol, etc., aromatic hydrocarbons such as benzene, toluene, etc., ethers such as tetrahydrofuran, dioxane, diglyme, etc., dimethyl sulfoxide, dimethylformamide, hexamethylphosphoric triamide, pyridine, etc.

The tertiary nitrogen containing aromatic heterocyclic compound or trialkylamine, and anion donating compound can be used in excess amounts over the equimolar amount relative to the compounds of the formula (Ia), preferably in an amount of from 1 to 2 mols per mol of the formula (Ia).

The reaction can usually be carried out at room temperature to about 120° C., preferably 50° to 100° C. for 30 minutes to 6 hours.

The hydrolysis of the compound of the formula (Ib) thus obtained can be conducted in an appropriate solvent in the absence or presence of an acid hydrolyzing agent or an alkaline hydrolyzing agent, preferably in the presence of such agent.

Examples of suitable alkaline hydrolyzing agent which can be used in the above hydrolysis reaction include alkali metal hydroxides such as sodium hydroxide, potassium hydroxide, etc., alkaline earth metal hydroxides such as calcium hydroxide, etc., ammonium hydroxide, and carbonates of these metals and ammonium.

The hydrolysis of the compound of the formula (Ib) can also be conducted in an aqueous medium in the presence of a trialkylamine such as a lower trialkylamine, e.g., trimethylamine, triethylamine, etc.

Examples of suitable solvent which can be used include lower alcohols such as methanol, ethanol, isopropanol, etc., aromatic hydrocarbons such as benzene, toluene, etc., ethers such as tetrahydrofuran, dioxane, diglyme, etc., water, pyridine, dimethyl sulfoxide, dimethylformamide, hexamethylphosphoric triamide, etc.

The hydrolysis can usually be effected at about 20° to about 150° C., preferably 80° to 120° C. for 30 minutes to 6 hours. The above hydrolysis can be accelerated by the addition of a lower alcohol.

The compounds of this invention represented by the formula (I) prepared as described above can form pharmaceutically acceptable salts with acids and this invention also includes within its scope such pharmaceutically acceptable salts. The pharmaceutically acceptable acids which can be used for the salt formation can be various organic or inorganic acids, for example, hydrochloric acid, sulfuric acid, nitric acid, hydrobromic acid, phosphoric acid, acetic acid, oxalic acid, malonic acid, succinic acid, maleic acid, fumaric acid, malic acid, benzoic acid, mandelic acid, ethanesulfonic acid, p-toluenesulfonic acid and the like.

The benzoheterocyclic compounds of the formula (I) can be converted into a corresponding carboxylate by reacting the carboxylic acid with a pharmaceutically acceptable basic compound. Examples of basic compounds are inorganic basic compounds such as sodium hydroxide, potassium hydroxide, calcium hydroxide, aluminum hydroxide, sodium bicarbonate and the like and organic basic compounds such as morpholine, piperazine, pyridine, piperidine, ethylamine, dimethylamine, triethylamine, aniline and the like.

The compounds of the formula (I) and the salts thereof obtained as described above can be isolated from the respective reaction mixtures upon completion and purified by conventional procedures, for example, by solvent extraction, dilution, precipitation, recrystallization, column chromatography, preparative thin layer chromatography and the like.

The compounds of this invention of the formula (I) and the salts thereof are characterized by excellent antimicrobial activity broadly, on both gram positive and negative bacteria at low concentrations, a low toxicity and very weak side effects, if any. They are useful not only as a medicine for the therapy of diseases in humans, animals and fish caused by various bacteria but also as sterilizers or antiseptics for external application for medical tools and devices and the like.

They are useful compounds which show particularly potent antibacterial activity on gram positive bacteria such as staphylococci, and anaerobic bacteria and have excellent antimicrobial activity on those bacteria which are resistant or have acquired resistance to conventional antibiotics such as penicillin, cephalosporin, etc.

Further, the compounds of this invention can be excreted with ease into bile and therefore their toxicity is low and their activity is lasting for a long period of time.

In using the compounds of this invention of the formula (I) and the salts thereof as therapeutic agents, these compounds can be formulated into pharmaceutical compositions together with ordinary pharmaceutically acceptable carriers. Suitable carriers which can be used are, for example, diluents or excipients, such as fillers, extenders, binders, wetting agents, disintegrants, surface active agents and lubricants which are usually employed to prepare such drugs depending on the type of dosage forms.

Various dosage forms of the therapeutic agents as an antimicrobial agent can be selected according to the purpose of the therapy. Typical dosage forms which can be used are: tablets, pills, powders, liquid preparations, suspensions, emulsions, granules, capsules, suppositories, and injectable preparations (solutions, suspensions, etc.).

In molding a pharmaceutical composition containing the compounds of the formula (I) or the pharmaceutically acceptable salt thereof as an active ingredient into a tablet form, a wide range of carriers known in the art can be used. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan, produced by Atlas Powder Co.), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, adsorbents such as starch, lactose, kaolin, bentonite and colloidal silicic acid, and lubricants such as purified talc, stearic acid salts, boric acid powder, Macrogol (trade name for a polyethylene glycol, produced by Shinetsu Chemical Industry Co., Ltd.) and solid polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semisynthetic glycerides.

When the pharmaceutical composition is formulated into an injectable preparation, the resulting solution and suspension are preferably sterilized and isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent, e.g., as a nephritis treating agent in an amount sufficient to prepare isotonic solutions. The antimicrobial pharmaceutical composition may further contain ordinary dissolving aids, buffers, pain-alleviating agents, and preservatives, and optionally coloring agents, perfumes, flavors, sweeteners, and other drugs.

The amount of the compound of the formula (I) and the pharmaceutically acceptable salts thereof of this invention as an active ingredients to be incorporated into a pharmaceutical composition useful as an antimicrobial agent is not particularly limited, and can vary over a wide range. A suitable effective amount of the compound of the formula (I) and the pharmaceutically acceptable salts thereof of this invention is usually from about 1% to 70% by weight, and preferably from 5 to 50% by weight, based on the weight of the entire composition.

There is no particular restriction on the manner of using the therapeutic agent and the therapeutic agent can be administered by routes suitable for the particular forms of the therapeutic agent. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the therapeutic agent can be simply administered intramuscularly, intracutaneously, subcutaneously or intraperitoneally. The suppository is administered intrarectally and the ointment is coated on the skin.

The dosage of the antimicrobial agent is suitably selected according to the purpose of use, the symptoms, etc. Usually, a preferred dosage of the compound of this invention is about 0.2 mg to 100 mg/kg body wt/day in 3 or 4 doses/day.

I. ANTIMICROBIAL ACTIVITY

1. Test Method

The antimicrobial activity of the following test compounds on various test organisms listed below was determined by the serial dilution method on agar plate (Heart Infusion agar produced by Difco Co.) (see *CHEMOTHERAPY* 22, pp. 1126–1128 (1974)), and the minimum inhibitory concentrations (mcg/ml) obtained are shown in Tables 1, 2 and 3 below.

A sample of each test organism was prepared so that the population of the organism was $1 \times 10^8$ cells/ml (O.D. 660 m$\mu$ = 0.07 to 0.16) and $1 \times 10^6$ cells/ml (which was obtained by diluting 100 fold the above $1 \times 10^8$ cells/ml preparation).

2. Test Organisms

| No. | | | |
|---|---|---|---|
| No. 1 | Escherichia | Coli NIHJ | JC-2 (IFO 12734) |
| No. 2 | Klebsiella | pneumoniae | |
| No. 3 | Proteus | rettgeri | NIH 96 |
| No. 4 | Pseudomonas | aeruginosa | E-2 |
| No. 5 | Pseudomonas | putida | 12996 |
| No. 6 | Pseudomonas | aeruginosa | ATCC 10145 |
| No. 7 | Salmonella | typhi | 0-901 (NCTC 8393) |
| No. 8 | Shigella | sonnei | EW 33 |
| No. 9 | Serratia | marcescens | IFO 12648 |
| No. 10 | Staphylococcus | aureus | FDA 209 P |
| No. 11 | Streptococcus | pyogenes | IID S-23 |
| No. 12 | Bacillus | subtilis | PCI 219 |
| No. 13 | Bacillus | anthracis | |
| No. 14 | Bacillus | cereus | ATCC 11778 |
| No. 15 | Bacillus | cereus | IFO 3001 |
| No. 16 | Bacillus | cereus | IFO 3446 |
| No. 17 | Bacillus | pumilus | IFO 3813 |
| No. 18 | Bacillus | circulans | ATCC 8241 |
| No. 19 | Staphylococcus | aureus | ATCC 12692 |
| No. 20 | Staphylococcus | aureus | Newmann |
| No. 21 | Staphylocossus | aureus | Smith |
| No. 22 | Staphylococcus | aureus | IFO 3761 |
| No. 23 | Staphylococcus | aureus | IFO 3060 |
| No. 24 | Staphylococcus | aureus | No. 80 |
| No. 25 | Staphylococcus | aureus | E-46 |
| No. 26 | Staphylococcus | aureus | B-70 |
| No. 27 | Staphylococcus | aureus | B-5 |
| No. 28 | Staphylococcus | aureus | 7447 |
| No. 29 | Staphylococcus | aureus | No. 286 |
| No. 30 | Staphylococcus | aureus | 90124 |
| No. 31 | Staphylococcus | aureus | 50774 |
| No. 32 | Staphylococcus | epidermidis | ATCC 12228 |
| No. 33 | Staphylococcus | epidermidis | IFO 3762 |
| No. 34 | Micrococcus | luteus | ATCC 4698 |
| No. 35 | Micrococcus | lysodeikticus | IAM 1313 |
| No. 36 | Micrococcus | flavus | ATCC 10240a |
| No. 37 | Sarcina | lutea | PCI 1001 |
| No. 38 | Corynebacterium | diphteriae | |
| No. 39 | Pseudomonas | aeruginosa | NCTC 10490 |
| No. 40 | Peptococcus | asaccharolyticus | WAL 3218 |
| No. 41 | Bacteroides | thetaiotaomicron | WAL 2926 |

3. Test Compounds

| | |
|---|---|
| Compound 1: | 9-Fluoro-8-(4-hydroxy-1-piperidyl)-5-methyl-6,7-dihydro-1-oxo-1H,5H—benzo[ij]-quinolizine-2-carboxylic acid |
| Compound 2: | 9-Fluoro-8-morpholino-5-methyl-6,7-dihydro-1-oxo-1H,5H—benzo[ij]quinolizine-2-carboxylic acid |
| Compound 3: | 9-Fluoro-8-(4-acetyloxy-1-piperidyl)-5-methyl-6,7-dihydro-1-oxo-1H,5H—benzo[ij]-quinolizine-2-carboxylic acid |
| Compound 4: | 9-Fluoro-8-(1-piperidyl)-5-methyl-6,7-dihydro-1-oxo-1H,5H—benzo[ij]quinolizine-2-carboxylic acid |
| Compound 5: | 9-Fluoro-8-(4-dimethylamino-1-piperidyl)-5-methyl-6,7-dihydro-1-oxo-1H,5H—benzo[ij]-quinolizine-2-carboxylic acid |
| Compound 6: | 9-(1-Pyrrolidinyl)-8-fluoro-2-methyl-1,2-dihydro-6-oxo-pyrrolo[3,2,1-ij]quinoline-5-carboxylic acid |
| Compound 7: | 9-Morpholino-8-fluoro-2-methyl-1,2-dihydro-6-oxo-pyrrolo[3,2,1-ij]quinoline-5-carboxylic acid |
| Compound 8: | 9-(4-Trifluoromethyl-1-piperazinyl)-8-fluoro-2-methyl-1,2-dihydro-6-oxo-pyrrolo[3,2,1-ij]-quinoline-5-carboxylic acid hydrochloride |
| Compound 9: Comparison | 1-Ethyl-1,4-dihydro-7-methyl-4-oxo-1,8-naphthyridine-3-carboxylic acid |

TABLE 1

Minimum Inhibitory Concentration ($\mu$g/ml)

| Test Organism No. | Compound 1 | | Compound 9 | |
|---|---|---|---|---|
| | $1 \times 10^8$ | $1 \times 10^6$ | $1 \times 10^8$ | $1 \times 10^6$ |
| 1 | 0.39 | 0.39 | 3.13 | 3.13 |
| 2 | 0.39 | 0.39 | 1.56 | 1.56 |
| 3 | 0.2 | 0.1 | 1.56 | 1.56 |
| 4 | 6.25 | 6.25 | >100 | >100 |
| 5 | 6.25 | 6.25 | >100 | >100 |
| 6 | 3.13 | 3.13 | >100 | >100 |
| 7 | 0.1 | 0.05 | 3.13 | 3.13 |
| 8 | 0.2 | 0.2 | 3.13 | 3.13 |
| 9 | 1.56 | 0.78 | 3.13 | 3.13 |
| 10 | ≦0.05 | ≦0.025 | 50 | 50 |
| 11 | 0.78 | 0.39 | >100 | >100 |
| 12 | 0.024 | 0.024 | | |
| 13 | 0.05 | 0.05 | | |
| 14 | 0.10 | 0.10 | | |
| 15 | 0.10 | 0.10 | | |
| 16 | 0.10 | 0.10 | | |
| 17 | 0.024 | 0.024 | | |
| 18 | 0.024 | 0.024 | | |
| 19 | 0.05 | 0.05 | | |
| 20 | 0.05 | 0.024 | | |
| 21 | 0.05 | 0.05 | | |
| 22 | 0.10 | 0.024 | | |
| 23 | 0.10 | 0.05 | | |
| 24 | 0.05 | 0.024 | | |
| 25 | 0.05 | 0.05 | | |
| 26 | 0.05 | 0.024 | | |
| 27 | 0.024 | 0.024 | | |
| 28 | 0.05 | 0.05 | | |
| 29 | 0.10 | 0.05 | | |
| 30 | 0.10 | 0.10 | | |
| 31 | 0.05 | 0.05 | | |
| 32 | 0.05 | 0.05 | | |
| 33 | 0.39 | 0.20 | | |
| 34 | 0.20 | 0.10 | | |
| 35 | 0.20 | 0.10 | | |
| 36 | 0.39 | 0.20 | | |
| 37 | 0.39 | 0.39 | | |
| 38 | 0.05 | 0.05 | | |
| 40 | 1.56 | 0.78 | | |
| 41 | 6.25 | 1.56 | | |

TABLE 2

| Test Organism No. | Minimum Inhibitory Concentration (μg/ml) | | | | | | | |
|---|---|---|---|---|---|---|---|---|
| | Compound 2 | | Compound 3 | | Compound 4 | | Compound 5 | |
| | $1 \times 10^8$ | $1 \times 10^6$ | $1 \times 10^8$ | $1 \times 10^6$ | $1 \times 10^8$ | $1 \times 10^6$ | $1 \times 10^8$ | $1 \times 10^6$ |
| 1 | 0.2 | 0.1 | 0.39 | 0.39 | 1.56 | 1.56 | 0.2 | 0.2 |
| 2 | 0.2 | 0.2 | 0.39 | 0.39 | 1.56 | 1.56 | 0.2 | 0.1 |
| 3 | 0.1 | 0.05 | 0.2 | 0.2 | 1.56 | 1.56 | 0.39 | 0.2 |
| 4 | 6.25 | 3.13 | 6.25 | 6.25 | 25 | 12.5 | 6.25 | 6.25 |
| 5 | 6.25 | 3.13 | 6.25 | 6.25 | 25 | 25 | 6.25 | 6.25 |
| 6 | 3.13 | 3.13 | 6.25 | 3.13 | 12.5 | 12.5 | 6.25 | 3.13 |
| 7 | 0.1 | 0.05 | 0.1 | 0.1 | 0.39 | 0.39 | 0.2 | 0.2 |
| 8 | 0.1 | 0.1 | 0.2 | 0.2 | 0.78 | 0.78 | 0.2 | 0.2 |
| 9 | 0.78 | 0.39 | 3.13 | 1.56 | 12.5 | 6.25 | 1.56 | 0.78 |
| 10 | 0.05 | 0.025 | 0.05 | 0.05 | 0.05 | 0.05 | 0.05 | 0.05 |
| 11 | 0.78 | 0.78 | 0.78 | 0.78 | 1.56 | 0.78 | 0.78 | 0.39 |

TABLE 3

| Test Organism No. | | Minimum Inhibitory Concentration (μg/ml) | | |
|---|---|---|---|---|
| | | Compound 6 | Compound 7 | Compound 8 |
| 1 | $1 \times 10^8$ | 0.39 | 0.20 | 0.05 |
| | $1 \times 10^6$ | 0.20 | 0.20 | 0.024 |
| 2 | $1 \times 10^8$ | 0.20 | 0.20 | 0.05 |
| | $1 \times 10^6$ | 0.20 | 0.10 | 0.012 |
| 3 | $1 \times 10^8$ | 0.10 | 0.05 | 0.012 |
| | $1 \times 10^6$ | 0.05 | 0.05 | <0.006 |
| 4 | $1 \times 10^8$ | 1.56 | 1.56 | 0.39 |
| | $1 \times 10^6$ | 1.56 | 1.56 | 0.39 |
| 6 | $1 \times 10^8$ | 1.56 | 1.56 | 0.39 |
| | $1 \times 10^6$ | 1.56 | 1.56 | 0.39 |
| 7 | $1 \times 10^8$ | 0.10 | 0.024 | ≦0.006 |
| | $1 \times 10^6$ | 0.10 | 0.024 | ≦0.006 |
| 8 | $1 \times 10^8$ | 0.05 | 0.024 | 0.012 |
| | $1 \times 10^6$ | 0.024 | 0.024 | ≦0.006 |
| 9 | $1 \times 10^8$ | 0.78 | 0.39 | 0.2 |
| | $1 \times 10^6$ | 0.39 | 0.20 | 0.1 |
| 10 | $1 \times 10^8$ | 0.024 | 0.024 | 0.05 |
| | $1 \times 10^6$ | 0.024 | 0.024 | 0.024 |
| 11 | $1 \times 10^8$ | 0.78 | 0.78 | 0.78 |
| | $1 \times 10^6$ | 0.78 | 0.78 | 0.39 |
| 39 | $1 \times 10^8$ | 1.56 | 1.56 | 0.39 |
| | $1 \times 10^6$ | 1.56 | 1.56 | 0.39 |

This invention will be described in greater detail with reference to Reference Examples, Examples and Preparation Examples.

REFERENCE EXAMPLE 1

Acetic anhydride (70.2 g) was added portionwise to a solution of 50 g of 3-chloro-4-fluoroaniline in 150 ml of acetic acid. After stirring at room temperature for 30 minutes, the reaction mixture was poured into water to precipitate solids which were then collected by filtration. The solids were washed with water and dissolved in ethyl acetate. The ethyl acetate layer was washed with a dilute aqueous potassium carbonate solution and dried over magnesium sulfate. Removal of the solvent by distillation gave 62 g of 3-chloro-4-fluoroacetamide. m.p. 116°–117° C.

REFERENCE EXAMPLE 2

3-Chloro-4-fluoroaniline (10 g) and phthalic anhydride (10.2 g) were dissolved in 30 ml of DMF and the solution was heated under reflux for 2 hours. Water was added to the reaction mixture to precipitate crystals which were then collected by filtration. The crystals were dissolved in ethyl acetate and the resulting solution was washed with an aqueous sodium hydrogen-carbonate solution and dried over magnesium sulfate to give 14.4 g of N-(3-chloro-4-fluoro-1-phenyl)phthalimide. m.p. 192°–193° C.

REFERENCE EXAMPLE 3

A solution of 6.5 g of potassium nitrate in 25 ml of concentrated sulfuric acid was added to a solution of 10 g of 3-chloro-4-fluoroacetanilide in 35 ml of concentrated sulfuric acid dropwise in 30 minutes at 0° C. After completion of addition the resulting mixture was stirred at 0° C. for 1.5 hours. The reaction mixture was poured into 400 ml of ice water to precipitate crystals, which were then collected by filtration, washed with water and dried to give 12.3 g of 2-nitro-4-fluoro-5-chloroacetanilide. m.p. 111°–112° C.

REFERENCE EXAMPLE 4

With keeping the temperature at 15°–20° C., 14 g of N-(3-chloro-4-fluoro-1-phenyl)phthalimide was dissolved in 75 ml of concentrated sulfuric acid and a solution of 5.6 g of potassium nitrate in 20 ml of concentrated sulfuric acid was added to the solution dropwise in 30 minutes at −5° C. After stirring at −5° to 0° C. for 1 hour, the reaction mixture was poured into 1.5 liter of ice water to precipitate crystals which were collected by filtration. After washing with water, the crystals were dissolved in dichloromethane and dried over magnesium sulfate. Evaporation of the solvent gave 15.4 g of N-(2-nitro-4-fluoro-5-chloro-1-phenyl)phthalimide. m.p. 222°–224° C.

REFERENCE EXAMPLE 5

2-Nitro-4-fluoro-5-chloroacetanilide (12 g) of 4-hydroxypiperidine (25.8 g) were dissolved in 120 ml of DMF and the solution was stirred at 70° C. for 2 hours. Excessive 4-hydroxypiperidine and DMF were distilled off under reduced pressure and 50 ml of water was added to the residue to precipitate crystals which were collected by filtration and washed with water. Recrystallization from methanol-water and subsequently from isopropanol gave 14.2 g of 2-nitro-4-fluoro-5-(4-hydroxy-1-piperidyl)acetanilide.

| Elemental Analysis for $C_{13}H_{16}N_3O_4F$ | | | |
|---|---|---|---|
| | C | H | N |
| Calc'd (%): | 52.52 | 5.43 | 14.14 |
| Found (%): | 52.40 | 5.56 | 14.03 |

REFERENCE EXAMPLE 6

A solution of 10 g of 2-nitro-4-fluoro-5-(4-hydroxy-1-piperidyl)acetanilide and 9.5 g of potassium hydroxide in 3 ml of water was dissolved in 100 ml of methanol and the solution was refluxed for 30 minutes. After cooling, 50 ml of water was added to the reaction mixture to precipitate solids. After washing with water, the solids were recrystallized from isopropanol to give 7.8 g of 2-nitro-4-fluoro-5-(4-hydroxy-1-piperidyl)aniline.

| Elemental Analysis for $C_{11}H_{14}N_3O_3F$ | | | |
|---|---|---|---|
| | C | H | N |
| Calc'd (%): | 51.76 | 5.53 | 16.46 |
| Found (%): | 51.68 | 5.64 | 16.58 |

REFERENCE EXAMPLE 7

To a solution of 25 g of 2-nitro-4-fluoro-5-(4-hydroxy-1-piperidyl)acetanilide in 250 ml of concentrated hydrochloric acid was added at a time a solution of 57.2 g of stannous chloride dihydrate in 250 ml of concentrated hydrochloric acid. During the addition it was observed that the reaction temperature was elevated to 40° C. After allowing to cool with stirring for 1 hour, solids which precipitated were collected by filtration and dissolved in a small amount of water. Under ice cooling, the solution was rendered alkaline with an aqueous sodium hydroxide solution and extracted with dichloromethane. After drying over potassium carbonate the solvent was distilled off and n-hexane was added to the residue to form crystals. The crystals were collected by filtration and dried to give 15.6 g of 2-amino-4-fluoro-5-(4-hydroxy-1-piperidyl-)acetanilide.

| Elemental Analysis for $C_{13}H_{18}N_3O_2F$ | | | |
|---|---|---|---|
| | C | H | N |
| Calc'd (%): | 58.41 | 6.79 | 15.72 |
| Found (%): | 58.63 | 6.92 | 15.93 |

REFERENCE EXAMPLE 8

An aqueous sodium nitrite solution prepared by dissolving 0.77 g of sodium nitrite in 5 ml of water was added to a solution of 3.0 g of 2-amino-4-fluoro-5-(4-hydroxy-1-piperidyl)acetanilide in 10 ml of water and 30 ml of hydrochloric acid dropwise at 0° C., and the mixture was stirred for 2 minutes. Then, 2 drops of n-octanol and 0.96 g of copper powder were added at a time. After stirring for 30 minutes, the reaction mixture was poured into water, rendered alkaline with an aqueous sodium hydroxide and extracted with dichloromethane. The extract was dried over magnesium sulfate and after distilling off the solvent the residue was purified through a silica gel column chromatography (chloroform:methanol=4:1) to give 0.87 g of 3-(4-hydroxy-1-piperidyl)-4-fluoroacetanilide.

| Elemental Analysis for $C_{13}H_{17}N_2O_2F$ | | | |
|---|---|---|---|
| | C | H | N |
| Calc'd (%): | 61.89 | 6.79 | 11.11 |
| Found (%): | 61.76 | 6.90 | 11.00 |

REFERENCE EXAMPLE 9

3-(4-Hydroxy-1-piperidyl)-4-fluoroacetanilide (0.80 g) was added to a solution of 0.60 g of silver sulfate in 10 ml of concentrated sulfuric acid with stirring. Then, 0.61 g of bromine was added to the mixture followed by stirring at an internal temperature of 30° to 40° C. for 1 hour. The reaction mixture was poured in water and insoluble substances were removed by filtration. The filtrate was rendered alkaline by the addition of an aqueous sodium hydroxide solution and extracted with dichloromethane. After concentration, the extract was purified through a silica gel column chromatography (chloroform:methanol=8:1) to give 0.16 g of 2-bromo-4-fluoro-5-(4-hydroxy-1-piperidyl)acetanilide.

| Elemental Analysis for $C_{13}H_{16}N_2O_2FBr$ | | | |
|---|---|---|---|
| | C | H | N |
| Calc'd (%): | 47.15 | 4.87 | 8.46 |
| Found (%): | 47.03 | 4.94 | 8.57 |

REFERENCE EXAMPLE 10

2-Bromo-4-fluoro-5-(4-hydroxy-1-piperidyl)acetanilide (0.10 g) was added to 5 ml of 47% hydrobromic acid and the mixture was refluxed for 1 hour. After distilling off 47% hydrobromic acid the residue was rendered alkaline by the addition of an aqueous sodium hydroxide solution to precipitate white solids which were collected by filtration and dried to give 0.07 g of 2-bromo-4-fluoro-(4-hydroxy-1-piperidyl)aniline.

| Elemental Analysis for $C_{11}H_{14}N_2OFBr$ | | | |
|---|---|---|---|
| | C | H | N |
| Calc'd (%): | 45.69 | 4.88 | 9.69 |
| Found (%): | 45.55 | 4.92 | 9.78 |

REFERENCE EXAMPLE 11

A solution of 11.5 g of potassium nitrate in 30 ml of concentrated sulfuric acid was added to 21.0 g of 5-bromo-6-fluoroquinaldine in 117 ml of concentrated sulfuric acid dropwise at −5° C. After stirring at room temperature for 5 hours, the reaction mixture was poured into 2 l of ice water to precipitate solids which were then collected by filtration. The filtrate was rendered alkaline to form a small amount of solids, which together with the former solids were dissolved in dichloromethane. After the solution was dried over sodium sulfate the solvent was distilled off. Recrystallization of the residue from isopropanol gave 22.9 g of 5-bromo-6-fluoro-8-nitroquinaldine. m.p. 135°–137° C.

| Elemental Analysis for $C_{10}H_6N_2O_2FBr$ | | | |
|---|---|---|---|
| | C | H | N |
| Calc'd (%): | 42.13 | 2.12 | 9.83 |
| Found (%): | 42.01 | 2.07 | 9.65 |

REFERENCE EXAMPLE 12

5-Bromo-6-chloroquinaldine (40 g) was dissolved in 220 ml of concentrated sulfuric acid. After cooling to 0° C., a solution of 20.5 g of potassium nitrate in 60 ml of concentrated sulfuric acid was added dropwise to the resulting solution in 30 minutes followed by stirring at room temperature for 2.5 hours. The reaction mixture was poured into 1.5 l of ice water and crystals which formed were collected by filtration. The filtrate was rendered alkaline to give a small amount of solids which together with the former solids were recrystallized from isopropanol to give 42.3 g of 5-bromo-6-chloro-8-nitroquinaldine. m.p. 141°–142° C.

| Elemental Analysis for $C_{10}H_6N_2O_2BrCl$ | | | |
|---|---|---|---|
| | C | H | N |
| Calc'd (%): | 39.83 | 2.00 | 9.29 |
| Found (%): | 39.97 | 1.92 | 9.14 |

REFERENCE EXAMPLE 13

2-Nitro-4-fluoro-5-(4-hydroxy-1-piperidyl)aniline (20 g) was added to 60% sulfuric acid prepared from 40 ml of concentrated sulfuric acid and 48 ml of water, and 13.2 g of sodium m-nitrobenzenesulfonate was added to the mixture. The resulting mixture was dissolved by heating to 110° C. and 6.6 g of crotonaldehyde was added dropwise to the solution in 10 minutes. After 5 minutes, the reaction mixture was poured in 30 ml of ice water to give 5-(4-hydroxy-1-piperidyl)-6-fluoro-8-nitroquinaldine, to which without isolation was added a solution of 71 g of stannous chloride dihydrate in 140 ml of concentrated hydrochloric acid and the mixture was stirred for 30 minutes. After treatment with activated carbon the reaction mixture was rendered alkaline with an aqueous sodium hydroxide solution to form precipitations which were extracted with dichloromethane. After distilling off the solvent isopropanol was added to the residue to dissolve it. Concentrated hydrochloric acid was added to the solution to form hydrochloric acid salt which was well washed with acetone and dissolved in water. The aqueous solution was rendered alkaline with an aqueous sodium hydroxide solution to precipitate solids which were collected by filtration to give 8.5 g of 5-(4-hydroxy-1-piperidyl)-6-fluoro-8-aminoquinaldine.

| Elemental Analysis for $C_{15}H_{18}N_3OF$ | | | |
|---|---|---|---|
| | C | H | N |
| Calc'd (%): | 65.44 | 6.59 | 15.26 |
| Found (%): | 65.58 | 6.73 | 15.12 |

REFERENCE EXAMPLE 14

To 1.5 g of 5-(4-hydroxy-1-piperidyl)-6-fluoro-8-amino-quinaldine were added 10 ml of concentrated hydrochloric acid and 3 ml of water, and 2 ml of an aqueous solution of 0.39 g of sodium nitrite was added dropwise to the mixture at −2° C. After 3 minutes one drop of n-octanol (defoaming agent) was added to the mixture. Then, 5.7 g of hypophosphorous acid (50% aqueous solution) already cooled to 0° C. was added dropwise to the mixture at −2° C. Thereafter, stirring was continued at 0°–5° C. for 7 hours. The reaction mixture was poured into water, rendered alkaline with an aqueous sodium hydroxide solution and extracted with dichloromethane. The extract was dried over sodium sulfate and the solvent was distilled off to give 0.68 g of 5-(4-hydroxy-1-piperidyl)-6-fluoroquinaldine.

| Elemental Analysis for $C_{15}H_{17}N_2OF$ | | | |
|---|---|---|---|
| | C | H | N |
| Calc'd (%): | 69.21 | 6.58 | 10.76 |
| Found (%): | 69.10 | 6.39 | 10.92 |

REFERENCE EXAMPLE 15

5-(4-Hydroxy-1-piperidyl)-6-fluoro-8-aminoquinaldine (2.0 g) was dissolved in 7 ml of water and 20 ml of concentrated hydrochloric acid and 0.53 g of sodium nitrite in 3 ml of an aqueous solution was added dropwise to the solution at 0° C. After 5 minutes, one drop of n-octanol (defoaming agent) and then 0.46 g of copper powder were added to the mixture at a time. Foaming was observed immediately. After foaming stopped the reaction mixture was stirred for additional 3 minutes at 0°–5° C. The reaction mixture was diluted with water and rendered alkaline with an aqueous sodium hydroxide solution to precipitate solids which were then collected by filtration and dissolved in mixed solvent of methanol-chloroform to remove insoluble substances. After concentration, the residue was purified through silica gel column chromatography (chloroform:methanol=5:1) to give 1.62 g of 5-(4-hydroxy-1-piperidyl)-6-fluoro-8-chloroquinaldine.

| Elemental Analysis for $C_{15}H_{16}N_2OClF$ | | | |
|---|---|---|---|
| | C | H | N |
| Calc'd (%): | 61.12 | 5.47 | 9.50 |
| Found (%): | 61.33 | 5.49 | 9.42 |

REFERENCE EXAMPLE 16

5-Bromo-6-fluoro-8-nitroquinaldine (9.0 g) and morpholine (13.7 g) were dissolved in 90 ml of DMF and the solution was stirred at an internal temperature of 70° C. for 6.5 hours. Excessive morpholine and DMF were distilled off under reduced pressure and n-hexane was added to the residue followed by sufficient stirring. Then, isopropanol was added to the solution to precipitate solids which then was collected by filtration. The solids were dissolved in water and the aqueous solution was rendered alkaline with an aqueous sodium hydroxide solution to precipitate solids, which were collected by filtration to give 3.3 g of 5-morpholino-6-fluoro-8-nitroquinaldine.

| Elemental Analysis for $C_{14}H_{14}N_3O_3F$ | | | |
|---|---|---|---|
| | C | H | N |
| Calc'd (%): | 57.73 | 4.84 | 14.43 |
| Found (%): | 57.62 | 4.98 | 14.29 |

REFERENCE EXAMPLE 17

Stannous chloride dihydrate (5.7 g) was added to a solution of 1.8 g of 5-morpholino-6-fluoro-8-nitroquinaldine in 30 ml of acetic acid and 20 ml of concentrated hydrochloric acid was added dropwise to the mixture with stirring. After completion of addition the mixture was stirred at room temperature for 1 hour, diluted with water and rendered alkaline with an aqueous sodium hydroxide solution to form precipitations, which then were extracted with dichloromethane, after drying over magnesium sulfate the solvent was distilled off to give 1.30 g of 5-morpholino-6-fluoro-8-aminoquinaldine.

| Elemental Analysis for $C_{14}H_{16}N_3OF$ | | | |
|---|---|---|---|
| | C | H | N |
| Calc'd (%): | 64.35 | 6.17 | 16.08 |

-continued

Elemental Analysis for $C_{14}H_{16}N_3OF$

|  | C | H | N |
|---|---|---|---|
| Found (%): | 64.51 | 6.03 | 16.89 |

REFERENCE EXAMPLE 18

5-(4-Hydroxy-1-piperidyl)-6-fluoroquinaldine (3.7 g) was dissolved in a mixed solvent consisting of 100 ml of acetic acid and 10 ml of ethyl acetate, and 1 g of 5% palladium-carbon was added to the mixture which then was placed in a vitrified autoclave. The reaction mixture was stirred at room temperature under a hydrogen gas pressure of 5 kg/cm$^2$ for 3 hours. After removing hydrogen gas the reaction mixture was taken out. After removing the catalyst, the content was concentrated to dryness, dissolved in 100 ml of chloroform and neutralized with 50 ml of an aqueous 5% sodium hydroxide solution. After separation and washing with 100 ml of water twice, the chloroform layer was dried and concentrated to dryness. To the residue were added 20 ml of hexane and 0.5 g activated carbon and the mixture was heated to dissolve. After removing activated carbon by filtration the hexane layer was cooled to precipitate crystals which then were collected to give 3.4 g of 5-(4-hydroxy-1-piperidyl)-6-fluoro-1,2,3,4-tetrahydroquinaldine.

Elemental Analysis for $C_{14}H_{21}N_2OF$

|  | C | H | N |
|---|---|---|---|
| Calc'd (%): | 66.64 | 8.39 | 11.10 |
| Found (%): | 66.78 | 8.51 | 11.02 |

REFERENCE EXAMPLE 19

In an analogous manner as in Reference Example 18 was prepared 5-morpholino-6-fluoro-1,2,3,4-tetrahydroquinaldine from 5-morpholino-6-fluoro-8-chloro-1,2,3,4-tetrahydroquinaldine.

Elemental Analysis for $C_{14}H_{19}N_2OF$

|  | C | H | N |
|---|---|---|---|
| Calc'd (%): | 67.18 | 7.65 | 11.19 |
| Found (%): | 67.32 | 7.78 | 11.27 |

REFERENCE EXAMPLE 20

A solution of 145 g of 2-bromo-4-fluoro-5-morpholinoaniline in 1 l of methylene chloride and the solution was cooled to a temperature of not higher than −50° C. on a dry ice-acetone bath. At the same temperature as above 60 g of tert-butyl hypochlorite was added dropwise to the solution during which operation the reaction system changed from heterogeneous mixture to homogeneous solution. Then, 67 g of methylthio-2-propanone was added dropwise to the solution and the mixture was reacted at the same temperature as above for 2 hours followed by adding dropwise 80 ml of triethylamine. After completion of addition, the temperature of the mixture was elevated slowly to room temperature. After room temperature was attained 1 l of water was added to separate the methylene chloride layer which then was dried over sodium sulfate and concentrated under reduced pressure to give 150 g of 2-methyl-3-methylthio-5-fluoro-4-morpholino-7-bromoindole.

Elemental Analysis for $C_{14}H_{16}N_2OSFBr$

|  | C | H | N |
|---|---|---|---|
| Calc'd (%): | 46.81 | 4.49 | 7.80 |
| Found (%): | 46.97 | 4.34 | 7.72 |

REFERENCE EXAMPLE 21

A solution of 800 g of 2-bromo-4-fluoro-5-morpholinoaniline in 4 l of dry methylene chloride was cooled to −60° C. and a solution of 350 g of tert-butyl hypochlorite in 500 ml of methylene chloride and then a solution of 680 g of ethylthio-2-propanone in 1 l of dichloromethane were added dropwise thereto at the same temperature as above. After completion of addition, the mixture was allowed to react at the same temperature as above for 2 hours, and then a solution of 325 g of triethylamine in 1 l of methylene chloride was added dropwise to the reaction mixture. After completion of addition the temperature of the reaction mixture was elevated slowly to room temperature, then, 5 l of water was added to the reaction mixture to separate the methylene chloride layer which was dried over magnesium sulfate. After concentration under reduced pressure 0.95 kg of 2-methyl-3-ethylthio-4-morpholino-5-fluoro-7-bromoindole was obtained.

Elemental Analysis for $C_{15}H_{18}N_2OSFBr$

|  | C | H | N |
|---|---|---|---|
| Calc'd (%): | 48.26 | 4.86 | 7.50 |
| Found (%): | 48.38 | 4.75 | 7.36 |

REFERENCE EXAMPLE 22

Raney nickel (1.5 kg) was added to a solution of 214 g of 2-methyl-3-methylthio-4-morpholino-5-fluoro-7-bromoindole in 3 l of ethanol and the mixture was refluxed for 3 hours. After completion of reaction the reaction mixture was cooled and Raney nickel was removed by filtration. Concentration of the filtrate gave 101 g of 2-methyl-4-morpholino-5-fluoroindole.

Elemental Analysis for $C_{13}H_{15}N_2OF$

|  | C | H | N |
|---|---|---|---|
| Calc'd (%): | 66.65 | 6.45 | 11.96 |
| Found (%): | 66.53 | 6.55 | 11.83 |

REFERENCE EXAMPLE 23

Raney nickel (400 g) was added to a solution of 58 g of 2-methyl-3-methylthio-4-morpholino-5-fluoro-7-bromoindole in 1 l of dioxane and the mixture was allowed to react at room temperature for 4 hours. After completion of the reaction Raney nickel was removed by filtration, and the filtrate was concentrated under reduced pressure. 33 g of 2-methyl-4-morpholino-5-fluoro-7-bromoindole was obtained.

Elememtal Analysis for $C_{13}H_{14}N_2OFBr$

|  | C | H | N |
|---|---|---|---|
| Calc'd (%): | 49.86 | 4.51 | 8.95 |

-continued

Elememtal Analysis for $C_{13}H_{14}N_2OFBr$

| | C | H | N |
|---|---|---|---|
| Found (%): | 49.92 | 4.63 | 8.82 |

REFERENCE EXAMPLE 24

To a solution of 24 g of 2-methyl-4-morpholino-5-fluoro-7-bromoindole in 200 ml of ethanol was added 1 g of palladium-carbon and then 15 ml of a 20% aqueous sodiium hydroxide solution. This mixture was subjected to catalytic reduction at room temperature and at atmospheric pressure. The reaction was stopped when a theoretical amount (about 1.7 l) of hydrogen was absorbed, and the catalyst was removed by filtration followed by concentration. The residue was purified through silica gel column chromatography (Wako gel C-200; eluent:chloroform:n-hexane=5:1) to give 11.8 g of 2-methyl-4-morpholino-5-fluoroindole.

Elemental Analysis for $C_{13}H_{15}N_2OF$

| | C | H | N |
|---|---|---|---|
| Calc'd (%): | 66.65 | 6.45 | 11.96 |
| Found (%): | 66.53 | 6.38 | 11.78 |

REFERENCE EXAMPLE 25

2-Methyl-5-fluoro-4-morpholinoindole (138 g) was dissolved in 1.5 l of acetic acid. To this solution was added 200 g of metal tin and the mixture was under reflux of acetic acid. During reflux 1.5 l of concentrated hydrochloric acid was added dropwise in 1 hour. After completion of addition, the mixture was allowed to react for 2 hours at the same temperature as above. After completion of reaction, the solvent was distilled off under reduced pressure. To the residue was added 1 l of water and the solution was adjusted to pH 13 with a 20% aqueous sodium hydroxide solution followed by adding 1 l of ether. After stirring insoluble substances were removed by filtration. An ether layer was separated from the filtrate and dried over anhydrous potassium carbonate. Removal of ether by distillation gave 75 g of 2-methyl-4-morpholino-5-fluoroindoline.

Elemental Analysis for $C_{13}H_{17}N_2OF$

| | C | H | N |
|---|---|---|---|
| Calc'd (%): | 66.08 | 7.25 | 11.86 |
| Found (%): | 66.13 | 7.46 | 11.71 |

REFERENCE EXAMPLE 26

Anhydrous piperidine (8 g) was added to 5.3 g of 8-chloro-9-fluoro-5-methyl-2-acetyl-6,7-dihydro-1-oxo-1H,5H-benzo[ij]quinolizine. 70 ml of hexamethylphosphoric triamide was added thereto and the mixture was allowed to react at 140° C. on an oil bath for 6 hours. After completion of the reaction any excess solvent and piperidine were removed by distillation under reduced pressure and 100 ml of ethyl acetate was added to the residue to precipitate light yellow crystals. The crystals thus obtained were separated by filtration and 300 ml of water was added thereto followed by adjusting the resulting solution to a pH of 2 with 1 N hydrochloric acid. The solution was heated and filtered. The filtrate was concentrated to 50 ml and rendered alkaline with a 10% aqueous sodium hydroxide solution to obtain 3.0 g of 8-(1-piperidyl)-9-fluoro-5-methyl-2-acetyl-6,7-dihydro-1-oxo-1H,5H-benzo[ij]quinolizine.

Elemental Analysis for $C_{20}H_{25}N_2OF$

| | C | H | N |
|---|---|---|---|
| Calc'd (%): | 73.14 | 7.67 | 8.53 |
| Found (%): | 73.36 | 7.76 | 8.41 |

REFERENCE EXAMPLE 27

2-Amino-4-fluoro-5-(4-hydroxy-1-piperazinyl)acetanilide (1.94 g) was dissolved in 7 ml of water and 20 ml of hydrobromic acid. To the solution was added dropwise 0.53 g of sodium nitrite in 3 ml of aqueous solution at 0° C. After 5 minutes, one drop of n-octanol (defoamant) was added to the mixture and subsequently 0.46 g of copper powder was added at a time thereto. Immediately foaming occurred. After foaming was over, the reaction mixture was stirred for additional 3 minutes at 0° to 5° C. The reaction mixture was diluted with water and rendered alkaline with aqueous sodium hydroxide solution to precipitate crystals, which were collected by filtration and dissolved in a mixed solvent consisting of methanol and chloroform to remove impurities. After concentrating, the residue was subjected to silica gel column chromatography to purify. Thus, 1.6 g of 2-bromo-4-fluoro-5-(4-hydroxy-1-piperazinyl)acetanilide was obtained. m.p. 126°–127° C.

EXAMPLE 1

In a 100 ml flask were placed 7.5 g of 9-fluoro-8-bromo-5-methyl-6,7-dihydro-1-oxo-1H,5H-benzo-[ij]-quinolizine-2-carboxylic acid, 9.5 g of 4-hydroxypiperidine and 60 ml of N-methyl-pyrrolidone and the mixture was stirred at 150° C. in a nitrogen gas atmosphere. After 6.5 hours disappearance of the starting materials was confirmed by thin layer chromatography, and N-methylpyrrolidone and 4-hydroxypiperidine were removed using an aspirator at a bath temperature of 140° to 150° C. To the residue were added dimethylformamide, ethanol and water and the mixture was allowed to stand overnight. On the next day, 1.6 g of crystals were obtained which were recrystallized twice each from ethanol-water to give 1.05 g of 9-fluoro-8-(4-hydroxy-1-piperidyl)-5-methyl-6,7-dihydro-1-oxo-1H,5H-benzo[ij]quinolizine-2-carboxylic acid. m.p. 244°–247° C.

Elemental Analysis for $C_{19}H_{21}N_2O_4F$

| | C | H | N |
|---|---|---|---|
| Calc'd (%): | 63.32 | 5.87 | 7.78 |
| Found (%): | 63.28 | 5.76 | 7.89 |

EXAMPLE 2

In a 100 ml flask were placed 7 g of 9-fluoro-8-bromo-5-methyl-6,7-dihydro-1-oxo-1H,5H-benzo[ij]quinolizine-2-carboxylic acid, 10.2 g of 4-methylpiperidine and 60 ml of hexamethylphosphoric triamide and the mixture was stirred at 160° C. in nitrogen gas atmosphere. After 6.5 hours, disappearance of the starting materials was confirmed by thin layer chromatography, and hexamethylphosphoric triamide was removed using a vacuum pump. To the residue was added several drops of concentrated hydrochloric acid and then ethyl acetate to separate oily substances from crystals. The crystals were collected by filtration and recrystallized from dimethylformamide-water to give 200 mg of 9-fluoro-8-(4-methyl-1-piperidyl)-5-methyl-6,7-dihydro-1-oxo-1H,5H-benzo[ij]quinolizine-2-carboxylic acid. m.p. 266° to 268° C., white rhombic crystals.

| Elemental Analysis for $C_{20}H_{23}N_2O_3F$ | | | |
|---|---|---|---|
| | C | H | N |
| Calc'd (%): | 67.02 | 6.47 | 7.82 |
| Found (%): | 66.93 | 6.41 | 7.91 |

EXAMPLE 3

In a 200 ml autoclave were placed 5 g of 9-fluoro-8-bromo-5-methyl-6,7-dihydro-1-oxo-1H,5H-benzo[ij]-quinolizine-2-carboxylic acid, 5 g of piperidine and 45 ml of hexamethylphosphoric triamide and the mixture was stirred at 160° C. After 5.5 hours, the temperature was lowered to room temperature and disappearance of the starting materials was confirmed by thin layer chromatography followed by removing hexamethylphosphoric triamide using a vacuum pump (120° C./2 mm Hg). To the residue was added several drops of concentrated hydrochloric acid and then ethyl acetate. Crystals which formed were collected by filtration and washed with ethyl acetate. The crystals thus obtained were recrystallized from dimethylformamide-water and the resulting crystals were added sodium hydroxide and water so as to obtain an aqueous solution of pH 13 which then was treated with activated carbon and filtered. The filtrate was adjusted to pH 7 with acetic acid to precipitate crystals which then were collected by filtration and recrystallized from dimethylformamide-water to give 570 mg of 9-fluoro-8-(1-piperidyl)-5-methyl-6,7-dihydro-1-oxo-1H,5H-benzo[ij]quinolizine-2-carboxylic acid. m.p. 258°-261° C., white rhombic crystals.

| Elemental Analysis for $C_{19}H_{21}N_2O_3F$ | | | |
|---|---|---|---|
| | C | H | N |
| Calc'd (%): | 66.26 | 6.15 | 8.14 |
| Found (%): | 66.31 | 6.02 | 8.23 |

EXAMPLE 4

In a 100 ml flask were placed 5 g of 9-fluoro-8-bromo-5-methyl-6,7-dihydro-1-oxo-1H,5H-benzo[ij]quinolizine-2-carboxylic acid, 6.8 g of 4-methoxy-1-piperidine and 45 ml of hexamethylphosphoric triamide and the mixture was stirred at 160° C. After 6.5 hours, disappearance of the starting materials was confirmed by thin layer chromatography and hexamethylphophoric triamide was removed using a vacuum pump (160° C./2 mm Hg). To the residue was added 3 drops of concentrated hydrochloric acid and then ethyl acetate. Crystals which formed were collected by filtration and washed with ethyl acetate. The crystals thus obtained were recrystallized from dimethylformamide-water and the resulting crystals were dissolved in an aqueous sodium hydroxide solution so as to obtain an aqueous solution of pH 13 which then was treated with activated carbon and filtered. The filtrate was adjusted to pH 7 with acetic acid to precipitate crystals which then were collected by filtration. Since disappearance of the starting material was confirmed by TLC. The crystals were dissolved in an aqueous sodium hydroxide solution to obtain a solution of pH 13 which then was adjusted to pH 7 with acetic acid. Recrystallization from dimethylformamide-water gave 1.5 g of 9-fluoro-8-(4-methoxy-1-piperidyl)-5-methyl-6,7-dihydro-1-oxo-1H,5H-benzo[ij]quinolizine-2-carboxylic acid. m.p. 249°-251° C., white rhombic crystals.

| Elemental Analysis for $C_{20}H_{23}N_2O_4F$ | | | |
|---|---|---|---|
| | C | H | N |
| Calc'd (%): | 64.16 | 6.19 | 7.48 |
| Found (%): | 64.01 | 6.23 | 7.31 |

EXAMPLE 5

In a 50 ml flask were placed 2.5 g of 9-fluoro-8-bromo-5-methyl-6,7-dihydro-1-oxo-1H,5H-benzo[ij]-quinolizine-2-carboxylic acid, 6.4 g of 4-benzylpiperidine and 25 ml of hexamethylphosphoric triamide and the mixture was stirred at 160° C. in an argon gas atmosphere for 7 hours. After disappearance of the starting materials was confirmed by thin layer chromatography, hexamethylphosphoric triamide was removed using a vacuum pump followed by cooling to room temperature. To the residue was added ethyl acetate and then several drops of concentrated hydrochloric acid and the mixture was allowed to stand in a refrigerator for 1 day. The crystals which formed were collected by filtration and recrystallized from dimethylformamide to give 0.45 g of 9-fluoro-8-(4-benzyl-1-piperidyl)-5-methyl-6,7-dihydro-1-oxo-1H,5H-benzo[ij]quinolizine-2-carboxylic acid. m.p. 230°-232° C., white rhombic crystals.

| Elemental Analysis for $C_{26}H_{27}N_2O_3F$ | | | |
|---|---|---|---|
| | C | H | N |
| Calc'd (%): | 71.87 | 6.26 | 6.45 |
| Found (%): | 71.68 | 6.45 | 6.32 |

EXAMPLE 6

In a 100 ml flask were placed 5 g of 9-fluoro-8-bromo-5-methyl-6,7-dihydro-1-oxo-1H,5H-benzo[ij]quinolizine-2-carboxylic acid, 9.4 g of nipecotamine and 45 ml of hexamethylphosphoric triamide and the mixture was stirred at 160° C. in an argon gas atmosphere for 7 hours. After disappearance of the starting materials was confirmed by thin layer chromatography, hexamethylphosphoric triamide was removed using a vacuum pump followed by lowering temperature to room temperature. To the residue was added ethyl acetate and then several drops of concentrated hydrochloric acid and the mixture was allowed to stand for 1 day. The crystal-like precipitations were washed with acetic acid and collected by filtration. Recrystallization from dimethylformamide gave 0.87 g of 9-fluoro-8-(3-carbamoyl-1-piperidyl)-5-methyl-6,7-dihydro-1-oxo-1H,5H-benzo[ij]quinolizine-2-carboxylic acid. m.p. not lower than 300° C., white rhombic crystals.

| Elemental Analysis for $C_{20}H_{22}N_3O_4F$ | | | |
|---|---|---|---|
| | C | H | N |
| Calc'd (%): | 62.00 | 5.73 | 10.85 |
| Found (%): | 61.90 | 5.78 | 10.76 |

EXAMPLE 7

In a 25 ml flask were placed 0.43 g of 9-fluoro-8-(4-hydroxy-1-piperidyl)-5-methyl-6,7-dihydro-1-oxo-1H,5H-benzo[ij]quinolizine-2-carboxylic acid, 0.2 g of acetic acid and 5 ml of dichloromethane and the mixture was refluxed after adding 5 drops of concentrated sulfuric acid. During the reaction oily substance appeared on the bottom of the flask. After 5 hours the reaction was stopped, dichloromethane was removed and water was added to the product followed by filtration. Crystals thus obtained were washed with methanol to give 150 mg of 9-fluoro-8-(4-acetoxy-1-piperidyl)-5-methyl-6,7-dihydro-1-oxo-1H,5H-benzo[ij]quinolizine-2-carboxylic acid. m.p. 250°–253° C., pale yellow rhombic crystals.

| Elemental Analysis for $C_{21}H_{23}N_2O_5F$ | | | |
|---|---|---|---|
| | C | H | N |
| Calc'd (%): | 62.67 | 5.76 | 6.96 |
| Found (%): | 62.53 | 5.87 | 6.78 |

EXAMPLE 8

In a 200 ml stainless steel autoclave were placed 10 g of 9-fluoro-8-bromo-5-methyl-6,7-dihydro-1-oxo-1H,5H-benzo[ij]quinolizine-2-carboxylic acid, 12.8 g of morpholine and 80 ml of hexamethylphosphoric triamide and the mixture was reacted at 160° C. on an oil bath. After 7 hours, the temperature of the autoclave was lowered to room temperature and disappearance of the starting materials was confirmed by thin layer chromatography. Then, the reaction mixture was transferred from the autoclave to a 300 ml Erlenmeyer flask to which ethyl acetate was added and the resulting mixture was allowed to stand for 1 day. The crystals which formed were collected by filtration and recrystallized from dimethylformamide to give 4 g of 9-fluoro-8-morpholino-5-methyl-6,7-dihydro-1-oxo-1H,5H-benzo[ij]quinolizine-2-carboxylic acid. m.p. 279°–280° C., white rhombic crystals.

| Elemental Analysis for $C_{18}H_{19}N_2FO_4$ | | | |
|---|---|---|---|
| | C | H | N |
| Calc'd (%): | 62.42 | 5.53 | 8.09 |
| Found (%): | 62.25 | 5.68 | 8.03 |

EXAMPLE 9

In a 100 ml flask were placed 6.1 g of 8-chloro-5-methyl-6,7-dihydro-1-oxo-1H,5H-benzo[ij]quinolizine-2-carboxylic acid, 9.5 g of 4-hydroxypiperidine and 60 ml of N-methylpyrrolidone and the mixture was stirred at 150° C. in an argon gas atmosphere. After 6 hours, N-methylpyrrolidone and excessive 4-hydroxypiperidine were removed under reduced pressure. To the residue were added dimethylformamide, ethanol and water and allowed to stand overnight to give 2.3 g of crude crystals which were recrystallized from ethanol-water to give 1.8 g of 8-(4-hydroxy-1-piperidyl)-5-methyl-6,7-dihydro-1-oxo-1H,5H-benzo[ij]quinolizine-2-carboxylic acid. m.p. 238°–240° C.

| Elemental Analysis for $C_{19}H_{22}N_2O_4$ | | | |
|---|---|---|---|
| | C | H | N |
| Calc'd (%): | 66.65 | 6.48 | 8.18 |
| Found (%): | 66.74 | 6.50 | 8.15 |

EXAMPLE 10

In an analogous manner as in Example 9, 1.5 g of 10-chloro-8-(4-hydroxy-1-piperidyl)-6,7-dihydro-1-oxo-1H,5H-benzo[ij]quinolizine-2-carboxylic acid was prepared from 6.6 g of 8,10-dichloro-6,7-dihydro-1-oxo-1H,5H-benzo[ij]quinolizine-2-carboxylic acid, 9.5 g of 4-hydroxypiperidine and 100 ml of N-methylpyrrolidone. m.p. 253°–256° C.

| Elemental Analysis for $C_{18}H_{19}O_4N_2Cl$ | | | |
|---|---|---|---|
| | C | H | N |
| Calc'd (%): | 59.59 | 5.28 | 7.72 |
| Found (%): | 59.42 | 5.12 | 7.84 |

EXAMPLE 11

In a 200 ml autoclave were placed 4.6 g of 8,9-dichloro-5-methyl-6,7-dihydro-1-oxo-1H,5H-benzo[ij]quinolizine-2-carboxylic acid, 5 g of piperidine and 50 ml of hexamethylphosphoric triamide and the mixture was reacted at 160° C. on an oil bath for 5 hours. After completion of reaction hexamethylphosphoric triamide and piperidine were distilled off under reduced pressure and to the residue was added ethyl acetate and crystallized. Recrystallization from dimethylformamide-water give 1.3 g of 9-chloro-8-(1-piperidyl)-5-methyl-6,7-dihydro-1-oxo-1H,5H-benzo[ij]quinolizine-2-carboxylic acid. m.p. 246° to 248° C.

| Elemental Analysis for $C_{19}H_{21}O_3N_2Cl$ | | | |
|---|---|---|---|
| | C | H | N |
| Calc'd (%): | 63.24 | 5.87 | 7.76 |
| Found (%): | 63.12 | 5.95 | 7.68 |

EXAMPLE 12

A mixture of 7 g of 9-fluoro-8-bromo-5-methyl-6,7-dihydro-1-oxo-1H,5H-benzo[ij]quinolizine-2-carboxylic acid, 12 g of 4-dimethylaminopiperidine and 50 ml of hexamethylphosphoric triamide was heated at 150° C. on an oil bath for 5 hours. After completion of reaction, hexamethylphosphoric triamide was distilled off under reduced pressure and to the residue was added ethyl acetate to form crystals. The crystals were suspended in 500 ml of water and a 47% aqueous hydrobromic acid was added thereto to adjust pH to 3 followed by heating. Then, insoluble substances were removed by filtration. The filtrate was concentrated and the residue was recrystallized from ethanol-water. Crystals which formed were dissolved in a 10% aqueous sodium hydroxide solution and the resulting solution was adjusted to pH 8 with dilute hydrochloric acid to precipitate white crystals, which then were dried to give 2.4 g of 9-fluoro-8-(4-dimethylamino-1-piperidyl)-5-methyl-6,7-dihydro-1-oxo-1H,5H-benzo[ij]quinolizine-2-carboxylic acid. m.p. 259°–261° C., white rhombic crystals.

| Elemental Analysis for $C_{21}H_{26}O_3N_3F$ | | | |
| --- | --- | --- | --- |
| | C | H | N |
| Calc'd (%): | 65.10 | 6.76 | 10.85 |
| Found (%): | 64.97 | 6.88 | 10.72 |

EXAMPLE 13

A mixture of 3.5 g of 9-fluoro-8-bromo-5-methyl-6,7-dihydro-1-oxo-1H,5H-benzo[ij]quinolizine-2-carboxylic acid, 6 g of 4-acetylaminopiperidine and 30 ml of hexamethylphosphoric triamide was heated at 150° C. for 4 hours. After completion of reaction, hexamethylphosphoric triamide was distilled off under reduced pressure, and the residue was recrystallized from dimethylformamide-water. Crystals which formed were again recrystallized from dimethylformamide to give 0.82 g of 9-fluoro-8-(4-acetylamino-1-piperidyl)-5-methyl-6,7-dihydro-1-oxo-1H,5H-benzo[ij]quinolizine-2-carboxylic acid. m.p. 274°–277° C., white rhombic crystals.

| Elemental Analysis for $C_{21}H_{24}O_4N_3F$ | | | |
| --- | --- | --- | --- |
| | C | H | N |
| Calc'd (%): | 62.83 | 6.03 | 10.47 |
| Found (%): | 62.78 | 6.15 | 10.42 |

EXAMPLE 14

A mixture of 2 g of 9-fluoro-8-(4-acetylamino-1-piperidyl)-5-methyl-6,7-dihydro-1-oxo-1H,5H-benzo[ij]quinolizine-2-carboxylic acid and 50 ml of a 10% aqueous sodium hydroxide solution was heated for 10 hours. After completion of reaction, the reaction mixture was cooled and adjusted to pH 4 with dilute hydrochloric acid (10%) to form precipitations, which then were recrystallized from ethanol-water to give 0.7 g of 9-fluoro-8-(4-amino-1-piperidyl)-5-methyl-6,7-dihydro-1-oxo-1H,5H-benzo[ij]quinolizine-2-carboxylic acid hydrochloride. m.p. not lower than 300° C., white rhombic crystals.

| Elemental Analysis for $C_{19}H_{22}O_3N_3F \cdot HCl$ | | | |
| --- | --- | --- | --- |
| | C | H | N |
| Calc'd (%): | 57.65 | 5.86 | 10.61 |
| Found (%): | 57.46 | 5.97 | 10.52 |

EXAMPLE 15

A mixture of 3 g of 9-fluoro-8-bromo-5-methyl-6,7-dihydro-1-oxo-1H,5H-benzo[ij]quinolizine-2-carboxylic acid, 5 g of 4-piperidineethylene acetate and 30 ml of hexamethylphosphoric triamide was heated at 160° C. on an oil bath for 6 hours. After completion of reaction, hexamethylphosphoric triamide was distilled off under reduced pressure, and to the residue was added ethyl acetate to precipitate crystals which then were recrystallized from dimethylformamide containing a small amount of dilute hydrochloric acid to give 0.87 g of 9-fluoro-8-(4-oxo-1-piperidyl)-5-methyl-6,7-dihydro-1-oxo-1H,5H-benzo[ij]quinolizine-2-carboxylic acid. m.p. not lower than 300° C., white rhombic crystals.

| Elemental Analysis for $C_{19}H_{19}O_4N_2F$ | | | |
| --- | --- | --- | --- |
| | C | H | N |
| Calc'd (%): | 63.68 | 5.34 | 7.82 |
| Found (%): | 63.62 | 5.45 | 7.73 |

EXAMPLE 16

A mixture of 3.4 g of 9-fluoro-8-bromo-5-methyl-6,7-dihydro-1-oxo-1H,5H-benzo[ij]quinolizine-2-carboxylic acid, 5 g of 3,5-dimethylpiperidine and 30 ml of hexamethylphosphoric triamide was heated at 150° C. on an oil bath for 5 hours. After completion of reaction, hexamethylphosphoric triamide was distilled off under reduced pressure. After having been recrystallized from dimethylformamide the residue was dissolved in a 10% aqueous sodium hydroxide solution and the resulting solution was adjusted to pH 7 with dilute hydrochloric acid (10%) to precipitate 9-fluoro-8-(3,5-dimethyl-1-piperidyl)-5-methyl-1-oxo-1H,5H-benzo[ij]quinolizine-2-carboxylic acid. This was dried at 70° C. for 12 hours to give 1.2 g of white rhombic crystals. m.p. 214°–216° C.

| Elemental Analysis for $C_{21}H_{25}N_2FO_3$ | | | |
| --- | --- | --- | --- |
| | C | H | N |
| Calc'd (%): | 67.72 | 6.77 | 7.52 |
| Found (%): | 67.68 | 6.82 | 7.48 |

EXAMPLE 17

An autoclave containing a mixture of 3 g of 9-fluoro-8-chloro-5-methyl-6,7-dihydro-1-oxo-1H,5H-benzo[ij]-quinolizine-2-carboxylic acid, 8 g of morpholine and 30 ml of hexamethylphosphoric triamide was immersed in an oil bath at 190° C. and reaction was continued for 5 hours. After completion of reaction, the reaction mixture was cooled to precipitate crystals which then were collected by filtration. The crystals thus obtained were recrystallized from dimethylformamide to give 0.77 g of 9-morpholino-8-chloro-5-methyl-6,7-dihydro-1-oxo-1H,5H-benzo[ij]quinolizine-2-carboxylic acid. m.p. 271° to 274° C., white rhombic crystals.

| Elemental Analysis for $C_{18}H_{19}N_2O_4Cl$ | | | |
| --- | --- | --- | --- |
| | C | H | N |
| Calc'd (%): | 59.59 | 5.28 | 7.72 |
| Found (%): | 59.53 | 5.35 | 7.61 |

EXAMPLE 18

A mixture of 56 g of 9-chloro-8-fluoro-2-methyl-1,2-dihydro-6-oxo-pyrrolo[3,2,1-ij]quinoline-5-carboxylic acid, 71 g of pyrrolidone and 60 ml of hexamethylphosphoric triamide in a stainless steel autoclave was reacted at 150° C. for 8 hours. After completion of reaction, hexamethylphosphoric triamide was distilled off under reduced pressure and the residue was recrystallized repeatedly from dimethylformamide to give 25 g of 9-(1-pyrrolidinyl)-8-fluoro-2-methyl-1,2-dihydro-6-oxo-pyrrolo[3,2,1-ij]quinoline-5-carboxylic acid. m.p. not lower than 300° C., pale yellow rhombic crystals.

| Elemental Analysis for $C_{17}H_{17}O_3N_2F$ | | | |
|---|---|---|---|
| | C | H | N |
| Calc'd (%): | 64.55 | 5.42 | 8.86 |
| Found (%): | 64.28 | 5.57 | 8.72 |

EXAMPLE 19

In an anlogous manner as in Example 1 the following compound was prepared:

9-(1,2,5,6-tetrahydro-1-pyridyl)-8-fluoro-2-methyl-1,2-dihydro-6-oxo-pyrrolo[3,2,1-ij]quinoline-5-carboxylic acid. m.p. 243°–245° C., pale yellow rhombic crystals.

| Elemental Analysis for $C_{18}H_{17}FN_2O_3$ | | | |
|---|---|---|---|
| | C | H | N |
| Calc'd (%): | 65.85 | 5.22 | 8.53 |
| Found (%): | 65.63 | 5.34 | 8.41 |

EXAMPLE 20

In an analogous manner as in Example 1, the following compound was prepared:

9-(4-hydroxy-1-piperidyl)-8-fluoro-2-methyl-1,2-dihydro-6-oxo-pyrrolo[3,2,1-ij]quinoline-5-carboxylic acid. m.p. 228°–231° C., white rhombic crystals.

| Elemental Analysis for $C_{18}H_{19}FN_2O_4$ | | | |
|---|---|---|---|
| | C | H | N |
| Calc'd (%): | 62.42 | 5.53 | 8.09 |
| Found (%): | 62.25 | 5.67 | 7.92 |

EXAMPLE 21

A mixture of 28 g of 9-chloro-8-fluoro-2-methyl-1,2-dihydro-6-oxo-pyrrolo[3,2,1-ij]quinoline-5-carboxylic acid, 5 g of thiomorpholine and 30 ml of hexamethylphosphoric triamide in a stainless steel autoclave was reacted at 150° C. for 7 hours. After completion of reaction, hexamethylphosphoric triamide was distilled off under reduced pressure and the residue was recrystallized from dimethylformamide to give 1.5 g of 9-thiomorpholino-8-fluoro-2-methyl-1,2-dihydro-6-oxo-pyrrolo[3,2,1-ij]quinoline-5-carboxylic acid. m.p. not lower than 300° C., slightly yellow rhombic crystals.

| Elemental Analysis for $C_{17}H_{17}FN_2O_3S$ | | | |
|---|---|---|---|
| | C | H | N |
| Calc'd (%): | 58.61 | 4.92 | 8.04 |
| Found (%): | 58.52 | 5.11 | 7.92 |

EXAMPLE 22

In an analogous manner as in Example 21 the following compound was prepared.

9-Morpholino-8-fluoro-2-methyl-1,2-dihydro-6-oxo-pyrrolo[3,2,1-ij]quinoline-5-carboxylic acid. m.p. 277°–280° C., white rhombic crystals.

| Elemental Analysis for $C_{17}H_{17}FN_2O_4$ | | | |
|---|---|---|---|
| | C | H | N |
| Calc'd (%): | 61.44 | 5.16 | 8.43 |

-continued

| Elemental Analysis for $C_{17}H_{17}FN_2O_4$ | | | |
|---|---|---|---|
| | C | H | N |
| Found (%): | 61.23 | 5.29 | 8.32 |

EXAMPLE 23

A mixture of 6 g of 9-chloro-8-fluoro-2-methyl-1,2-dihydro-6-oxo-pyrrolo[3,2,1-ij]quinoline-5-carboxylic acid, 8.6 g of 2-oxo-piperazine and 60 ml of hexamethylphosphoric triamide was reacted at 140°–150° C. on an oil bath for 6 hours. After completion of reaction, hexamethylphosphoric triamide was distilled off and to the residue was added ethyl acetate to form crystals, which then were collected by filtration. The crystals thus obtained were recrystallized twice each from dimethylformamide to give 2.4 g of 9-(3-oxo-1-piperazinyl)-8-fluoro-2-methyl-1,2-dihydro-6-oxo-pyrrolo[3,2,1-ij]quinoline-5-carboxylic acid. m.p. not lower than 300° C., white rhombic crystals.

| Elemental Analysis for $C_{17}H_{16}FN_3O_4$ | | | |
|---|---|---|---|
| | C | H | N |
| Calc'd (%): | 59.13 | 4.67 | 12.17 |
| Found (%): | 59.01 | 4.69 | 12.02 |

EXAMPLE 24

To a mixture of 3.3 g of 9-(1-piperazinyl)-8-fluoro-2-methyl-1,2-dihydro-6-oxo-pyrrolo[3,2,1-ij]quinoline-5-carboxylic acid and 20 ml of dimethylformamide was added 20 ml of a dimethylformamide solution of trifluoromethyl iodide containing 10 g of trifluoromethyl iodide, and the resulting mixture was reacted in a stainless steel autoclave on an oil bath at 110° to 120° C. for 5 hours. After completion of reaction, dimethylformamide was distilled off under reduced pressure and to the residue was added a 10% aqueous sodium hydroxide soluton so as to obtain a solution of pH 13. Insoluble substances were removed by filtration and the filtrate was adjusted to pH 3 with concentrated hydrochloric acid followed by concentration. Recrystallization of the residue from ethanol-water gave 1.8 g of 9-(4-trifluoromethyl-1-piperazinyl)-8-fluoro-2-methyl-1,2-dihydro-6-oxo-pyrrolo[3,2,1-ij]quinoline-5-carboxylic acid hydrochloride. m.p. now lower than 300° C., white rhombic crystals.

| Elemental Analysis for $C_{18}H_{18}ClF_4N_3O_3$ | | | |
|---|---|---|---|
| | C | H | N |
| Calc'd (%): | 49.61 | 4.16 | 9.65 |
| Found (%): | 49.75 | 4.32 | 9.42 |

EXAMPLES 25 TO 27

In an analogous manner as in Example 24, the following compounds were prepared.

EXAMPLE 25

9-(4-Trifluoromethyl-1-piperazinyl)-8-fluoro-2-ethyl-1,2-dihydro-6-oxo-pyrrolo[3,2,1-ij]quinoline-5-carboxylic acid hydrochloride. m.p. now lower than 300° C., white crystals.

| Elemental Analysis for $C_{19}H_{20}ClF_4N_3O_3$ | | | |
|---|---|---|---|
| | C | H | N |
| Calc'd (%): | 50.72 | 4.45 | 9.34 |
| Found (%): | 50.57 | 4.63 | 9.22 |

EXAMPLE 26

9-[4-(2,2,2-Trifluoroethyl)-1-piperazinyl]-8-fluoro-2-methyl-1,2-dihydro-6-oxo-pyrrolo[3,2,1-ij]quinoline-5-carboxylic acid hydrochloride. m.p. not lower than 300° C., white crystals.

| Elemental Analysis for $C_{19}H_{20}ClF_4N_3O_3$ | | | |
|---|---|---|---|
| | C | H | N |
| Calc'd (%): | 50.72 | 4.45 | 9.34 |
| Found (%): | 50.62 | 4.71 | 9.21 |

EXAMPLE 27

9-(4-Trifluoromethyl-1-piperazinyl)-8-fluoro-1,2-dihydro-6-oxo-pyrrolo[3,2,1-ij]quinoline-5-carboxylic acid hydrochloride. m.p. not lower than 300° C., white crystals.

| Elemental Analysis for $C_{17}H_{16}ClF_4N_3O_3$ | | | |
|---|---|---|---|
| | C | H | N |
| Calc'd (%): | 48.40 | 3.80 | 9.96 |
| Found (%): | 48.27 | 3.93 | 9.51 |

EXAMPLE 28

8,9-Difluoro-2-methyl-1,2-dihydro-6-oxo-pyrrolo[3,2,1-ij]quinoline-5-carboxylic acid (5 g) and a solution of 7.5 g of 3-hydroxypiperidine in 50 ml of hexamethylphosphoric triamide were reacted with heating at 120° to 130° C. for 7 hours with stirring. After completion of reaction, hexamethylphosphoric triamide and unreacted 3-hydroxypiperidine were distilled off under reduced pressure. Recrystallization of the residue from dimethylformamide gave 2.5 g of 8-fluoro-9-(3-hydroxy-1-piperidyl)-2-methyl-1,2-dihydro-6-oxo-pyrrolo[3,2,1-ij]quinoline-5-carboxylic acid. m.p. 251°–253° C.

| Elemental Analysis for $C_{18}H_{21}N_2O_3F$ | | | |
|---|---|---|---|
| | C | H | N |
| Calc'd (%): | 65.05 | 6.37 | 8.43 |
| Found (%): | 65.16 | 6.50 | 8.21 |

EXAMPLES 29 TO 31

In an analogous manner as in Example 28, the following compounds were prepared.

EXAMPLE 29

9-(2-Hydroxymethyl-1-pyrrolidinyl)-8-fluoro-2-methyl-1,2,-dihydro-6-oxo-pyrrolo[3,2,1-ij]quinoline-5-carboxylic acid. m.p. 235°–237° C., white rhombic crystals (DMF).

| Elemental Analysis for $C_{18}H_{19}N_2O_4F$ | | | |
|---|---|---|---|
| | C | H | N |
| Calc'd (%): | 62.42 | 5.53 | 8.09 |
| Found (%): | 62.27 | 5.36 | 8.16 |

EXAMPLE 30

9-[4-(2,2,2-Trifluoroethyl)-1-piperazinyl]-8-fluoro-2-methyl-1,2-dihydro-6-oxo-pyrrolo[3,2,1-ij]-quinoline-5-carboxylic acid. m.p. 287°–289° C., pale yellow rhombic crystals (dimethylformamide).

| Elemental Analysis for $C_{19}H_{19}N_3O_3F_4$ | | | |
|---|---|---|---|
| | C | H | N |
| Calc'd (%): | 55.21 | 4.63 | 10.17 |
| Found (%): | 55.18 | 4.78 | 10.26 |

EXAMPLE 31

9-Morpholino-8-fluoro-2-ethyl-1,2-dihydro-6-oxo-pyrrolo[3,2,1-ij]quinoline-5-carboxylic acid. m.p. 275°–278° C., pale yellow rhombic crystals (DMF).

EXAMPLE 32

(a) 4-[4-(2,2,2-Trifluoroethyl)-1-piperazinyl]-5-fluoro-2-methylindoline (12 g) and isopropylidenyl methoxymethylenemalonate (8 g) were mixed at room temperature and then heated at 100° C. for 30 minutes with stirring, during which operation the mixture was solidified. 13 g of cyclic isopropylidenyl N-{4-[4-(2,2,2-trifluoroethyl)-1-piperazinyl]-5-fluoro-2-methyl-1-indolinyl}aminomethylenemalonate was obtained.

| Elemental Analysis for $C_{22}H_{25}N_3O_4F$ | | | |
|---|---|---|---|
| | C | H | N |
| Calc'd (%): | 63.76 | 6.08 | 10.14 |
| Found (%): | 63.83 | 6.17 | 10.32 |

(b) 50 g of polyphosphoric acid prepared from 25 g of phosphorus pentoxide and 25 g of phosphoric acid and 13.0 g of cyclic isopropylidenyl N-{4-[4-(2,2,2-trifluoroethyl)-1-piperazinyl]-5-fluoro-2-methyl-1-indolinyl}-aminomethylenemalonate obtained in (a) above were heated at 100° C. for 1 hour with stirring. After cooling to 80° C., 60 ml of water was added to dissolve the product and the resulting solution was neutralized with a 20% aqueous sodium hydroxide solution followed by extracting with 200 ml of chloroform twice. The chloroform layer was dessicated over anhydrous magnesium sulfate and concentrated to dryness. To the crystals which formed was added 40 ml of dimethylformamide and 0.5 g of activated carbon and the mixture was heated to dissolve. After removing activated carbon the mixture was cooled to precipitate crystals, which then were collected by filtration to give 540 mg of 9-[4-(2,2,2-trifluoroethyl)-1-piperazinyl]-8-fluoro-2-methyl-1,2-dihydro-6-oxo-pyrrolo[3,2,1-ij]quinoline-5-carboxylic acid. m.p. 287°–289° C., pale yellow rhombic crystals.

EXAMPLES 33 TO 46

In an analogous manner as in Example 32, the same compounds as those obtained in Examples 18 to 31, respectively, were prepared using appropriate starting materials.

EXAMPLE 47

(a) A mixture of 9.3 g of 4-[4-(2,2,2-Trifluoroethyl-1-piperazinyl]-5-fluoro-2-methylindoline and 9 g of diethyl ethoxymethylenemalonate was heated at 160° C. for 30 minutes, during which operation the mixture was solidified. Recrystallization from dimethylformamide of the solid thus formed gave 13 g of diethyl N-{4-[4-(2,2,2-trifluoroethyl)-1-piperazinyl]-5-fluoro-2-methyl-1-indolinyl}aminomethylenemalonate.

| Elemental Analysis for $C_{22}H_{25}N_3O_4F$ | | | |
| --- | --- | --- | --- |
| | C | H | N |
| Calc'd (%): | 63.76 | 6.08 | 10.14 |
| Found (%): | 63.89 | 6.19 | 10.02 |

(b) 70 g of polyphosphoric acid prepared from 35 g of phosphorus pentoxide and 35 g of phosphoric acid and 13.0 g of diethyl N-{4-[4-(2,2,2-trifluoroethyl)-1-piperazinyl]-5-fluoro-2-methyl-1-indolinyl}aminomethylenemalonate obtained in (a) above were heated at 140°-150° C. for 1 hour. After completion of reaction the reaction mixture was poured into 200 g of ice water and adjusted to pH 6-7 with 10 N aqueous sodium hydroxide solution. Precipitations which formed were collected by filtration and added to 60 ml of concentrated hydrochloric acid followed by reacting by heating under reflux for 1 hour. After heating 100 ml of water was added to the reaction mixture to precipitate crystals, which then were collected by filtration, washed with water and dried. Recrystallization of the crystals from DMF gave 558 mg of 9-[4-(2,2,2-trifluoroethyl)-1-piperazinyl]-8-fluoro-2-methyl-1,2-dihydro-6-oxo-pyrrolo[3,2,1-ij]quinoline-5-carboxylic acid. m.p. 287°-289° C., pale yellow rhombic crystals.

EXAMPLES 48 TO 61

In an analogous manner as in Example 47, the same compounds as those obtained in Examples 18 to 31, respectively, were prepared using appropriate starting materials.

EXAMPLE 62

A mixture of 7.2 g of 4-[4-(2,2,2-trifluoroethyl-1-piperazinyl]-5-fluoro-2-methylindoline and 6.0 g of diethyl ethoxymethylenemalonate was reacted by heating at 160° C. for 30 minutes. Then, 48 g of polyphosphoric acid prepared from 24 g of phosphorus pentoxide and 24 g of phosphoric acid was added thereto and the resulting mixture was reacted by heating at 150°-160° C. for 1 hour. After completion of the reaction the reaction mixture was poured into 150 g of ice water. Precipitations which formed were collected by filtration, washed with water and dried. To the crystals thus obtained was added 70 ml of a 10% aqueous sodium hydroxide solution and the mixture was reacted at 100°-110° C. for 1 hour. After cooling the reaction mixture was rendered acidic with concentrated hydrochloric acid to precipitate crystals, which then were collected by filtration, washed with water and recrystallized from dimethylformamide to give 440 mg of 9-[4-(2,2,2-trifluoroethyl)1-piperazinyl]-8-fluoro-2-methyl-1,2-dihydro-6-oxo-pyrrolo[3,2,1-ij]quinoline-5-carboxylic acid. m.p. 287°-289° C., pale yellow rhombic crystals.

EXAMPLES 63 TO 76

In an analogous manner as in Example 62, the same compounds as those obtained in Examples 18 to 31, respectively, were prepared using appropriate starting materials.

EXAMPLE 77

(a) Iodine (3 g) and 20 ml of pyridine were added to 2.9 g of 8-(1-piperidyl)-9-fluoro-5-methyl-2-acetyl-6,7-dihydro-1-oxo-1H,5H-benzo[ij]quinolizine and the mixture was heated at 100° C. for 1 hour. After completion of the reaction, the crystals precipitated were separated by filtration and washed with 10 ml of cold pyridine and 10 ml of methanol to obtain 8-(1-piperidyl)-9-fluoro-5-methyl-6,7-dihydro-1-oxo-1H,5H-benzo[ij]quinolizine-2-carbonylmethylpyridinium iodide.

(b) The product obtained in (a) above was added in 50 ml of methanol and 50 ml of a 10% aqueous sodium hydroxide was added thereto and the mixture was refluxed for 1 hour. After completion of the reaction, methanol was removed by distillation under reduced pressure followed by adjusting the concentrate to pH 7 with 1 N hydrochloric acid to obtain 1.5 g of 8-(1-piperidyl)-9-fluoro-5-methyl-6,7-dihydro-1-oxo-1H,5H-benzo[ij]quinolizine-2-carboxylic acid. m.p. 258°-261° C., white rhombic crystals.

EXAMPLES 78 TO 94

In an analogous manner as in Example 77, the same compounds as those obtained in Examples 1 to 17, respectively, were prepared using appropriate starting materials.

EXAMPLE 95

(a) Iodine (3 g) and 20 ml of pyridine were added to 2.78 g of 9-(1-piperidyl)-8-fluoro-2-methyl-5-acetyl-1,2-dihydro-6-oxo-pyrrolo[3,2,1-ij]quinoline and the mixture was heated at 100° C. for 1 hour. After completion of the reaction, the crystals precipitated were separated by filtration and washed with 10 ml of cold pyridine and 10 ml of methanol to obtain 9-(1-piperidyl)8-fluoro-2-methyl-1,2-dihydro-6-oxo-pyrrolo[3,2,1-ij]quinoline-5-carbonylmethylpyridinium iodide.

(b) The product obtained in (a) above was added in 50 ml of methanol and 50 ml of a 10% aqueous sodium hydroxide was added thereto and the mixture was refluxed for 1 hour. After completion of the reaction, methanol was removed by distillation under reduced pressure followed by adjusting the concentrate to pH 7 with 1 N hydrochloric acid to obtain 1.8 g of 9-(1-piperidyl)-8-fluoro-2-methyl-1,2-dihydro-6-oxo-pyrrolo[3,2,1-ij]quinoline-5-carboxylic acid, m.p. not lower than 300° C., pale yellow rhombic crystals.

EXAMPLES 96 TO 109

In an analogous manner as in Example 95, the same compounds as those obtained in Examples 18 to 31, respectively, were prepared using appropriate starting materials.

EXAMPLE 110

(a) 5-(4-Hydroxy-1-piperidyl)-6-fluoro-2-methyl-1,2,3,4-tetrahydroquinaldine (10 g) and isopropylidenyl methoxymethylenemalonate (8 g) were mixed at room temperature and then heated at 100° C. for 30 minutes with stirring, during which operation the mixture was solidified. Recrystallization of the solid gave 14.5 g of cyclic isopropylidenyl N-[5-(4-hydroxy-1-piperidyl)6-fluoro-2-methyl-1,2,3,4-tetrahydro-1-quinaldinyl-]aminomethylenemalonate.

| Elemental Analysis for $C_{22}H_{27}N_2O_5F$ | | | |
| --- | --- | --- | --- |
| | C | H | N |
| Calc'd (%): | 63.15 | 6.50 | 6.70 |
| Found (%): | 63.28 | 6.63 | 6.57 |

(b) 50 g of polyphosphoric acid prepared from 25 g of phosphorus pentoxide and 25 g of phosphoric acid and 14.0 g of cyclic isopropylidenyl N-[5-(4-hydroxy-1-piperidyl)-6-fluoro-2-methyl-1,2,3,4-tetrahydro-1-quinaldinyl]aminomethylenemalonate obtained in (a) above were heated at 100° C. for 1 hour with stirring. After cooling to 80° C., 60 ml of water was added to dissolve the product and the resulting solution was neutralized with a 20% aqueous sodium hydroxide solution followed by extracting with 200 ml of chloroform twice. The chloroform layer was dessicated over anhydrous magnesium sulfate and concentrated to dryness. To the crystals which formed were added 40 ml of ethanol-water and 0.5 g of activated carbon and the mixture was heated to dissolve. After removing activated carbon, the mixture was cooled to precipitate crystals, which then were collected by filtration. Thus, 600 mg of 8-(4-hydroxy-1-piperidyl)9-fluoro-5-methyl-6,7-dihydro-1-oxo-1H,5H-benzo[ij]quinolizine-2-carboxylic acid was obtained. m.p. 244° to 247° C.

| Elemental Analysis for $C_{19}H_{21}O_4N_2F$ | | | |
| --- | --- | --- | --- |
| | C | H | N |
| Calc'd (%): | 63.32 | 5.87 | 7.78 |
| Found (%): | 63.25 | 5.79 | 7.90 |

EXAMPLES 111 TO 127

In an analogous manner as in Example 110, the same compounds as those obtained in Examples 1 to 17, respectively, were prepared using appropriate starting materials.

EXAMPLE 128

(a) 5-(4-Hydroxy-1-piperidyl-6-fluoro-2-methyl-1,2,3,4-tetrahydroquinaldine (7.6 g) and diethyl ethoxymethylenemalonate (9 g) were mixed and the mixture was heated at 160° C. for 30 minutes, during which operation the mixture was solidified. Recrystallization gave 11.3 g of diethyl N-[5-(4-hydroxy-1-piperidyl)-6-fluoro-2-methyl-1,2,3,4-tetrahydro-1-quinaldinyl-]aminomethylenemalonate.

| Elemental Analysis for $C_{22}H_{31}N_2O_5F$ | | | |
| --- | --- | --- | --- |
| | C | H | N |
| Calc'd (%): | 63.58 | 6.19 | 6.45 |
| Found (%): | 63.67 | 6.25 | 6.58 |

(b) 65 g of polyphosphoric acid prepared from 32.5 g of phosphorus pentoxide and 32.5 g of phosphoric acid and 11.3 g of diethyl N-[5-(4-hydroxy-1-piperidyl)6-fluoro-2-methyl-1,2,3,4-tetrahydro-1-quinaldinyl-]aminomethylenemalonate obtained in (a) above were heated at 140°-150° C. for 1 hour. After completion of reaction, the reaction mixture was poured into 200 g of ice water and adjusted to pH 6-7 with 10 N aqueous sodium hydroxide solution. Precipitations which formed were collected by filtration, and added to 60 ml of concentrated hydrochloric acid followed by reacting by heating under reflux for 1 hour. After heating 100 ml of water was added to the reaction mixture to precipitate crystals, which then were collected by filtration, washed with water and dried. Recrystallization from ethanol-water gave 480 mg of 8-(4-hydroxy-1-piperidyl)-9-fluoro-5-methyl-6,7-dihydro-1-oxo-1H,5H-benzo[ij]quinolizine-2-carboxylic acid. m.p. 244°-247° C.

| Elemental Analysis for $C_{19}H_{21}N_2O_4F$ | | | |
| --- | --- | --- | --- |
| | C | H | N |
| Calc'd (%): | 63.32 | 5.87 | 7.78 |
| Found (%): | 63.26 | 5.75 | 7.91 |

EXAMPLES 129 TO 145

In an analogous manner as in Example 128, the same compounds as those obtained in Examples 1 to 17, respectively, were prepared using appropriate starting materials.

EXAMPLE 146

A mixture of 6.6 g of 5-(4-hydroxy-1-piperidyl)-6-fluoro-2-methyl-1,2,3,4-tetrahydroquinaldine and 6.0 g of diethyl ethoxymethylenemalonate was reacted by heating at 160° C. for 30 minutes. Then, 48 g of polyphosphoric acid prepared from 24 g of phosphorus pentoxide and 24 g of phosphoric acid was added thereto and the resulting mixture was reacted by heating at 150°-160° C. for 1 hour. After completion of the reaction the reaction mixture was poured into 150 g of ice water. Precipitations which formed were collected by filtration, washed with water and dried. To the crystals thus obtained were added 70 ml of a 10% aqueous sodium hydroxide solution and the mixture was reacted at 100°-110° C. for 1 hour. After cooling, the reaction mixture was rendered acidic with concentrated hydrochloric acid to precipitate crystals, which then were collected by filtration, washed with water and recrystallized from ethanol-water to give 440 mg of 8-(4-hydroxy-1-piperidyl)-9-fluoro-5-methyl-6,7-dihydro-1-oxo-1H,5H-benzo[ij]quinolizine-2-carboxylic acid. m.p. 244°-247° C.

| Elemental Analysis for $C_{19}H_{21}N_2O_4F$ | | | |
| --- | --- | --- | --- |
| | C | H | N |
| Calc'd (%): | 63.32 | 5.87 | 7.78 |
| Found (%): | 63.27 | 5.77 | 7.92 |

EXAMPLES 147 TO 163

In an analogous manner as in Example 144, the same compounds as those obtained in Examples 1 to 17, respectively, were prepared using appropriate starting materials.

EXAMPLE 164

In an analogous manner as in Example 2, 9-fluoro-8-thiomorpholino-5-methyl-6,7-dihydro-1-oxo-1H,5H-benzo[ij]quinolizine-2-carboxylic acid was prepared from 9-fluoro-8-bromo-5-methyl-6,7-dihydro-1-oxo-1H,5H-benzo]ij]quinoline-2-carboxylic acid and thiomorpholine. m.p. 292°–294° C., white rhombic crystals (DMF).

EXAMPLE 165

In an analogous manner as in Example 2, 9-fluoro-8-(1-pyrrolidinyl)-5-methyl-6,7-dihydro-1-oxo-1H,5H-benzo[ij]quinolizine-2-carboxylic acid was prepared from 9-fluoro-8-bromo-5-methyl-6,7-dihydro-1-oxo-1H,5H-benzo[ij]quinoline-2-carboxylic acid and pyrrolidine. m.p. 248°–250° C., white rhombic crystals (DMF).

EXAMPLE 166

In an analogous manner as in Example 2, 9-chloro-8-morpholino-5-methyl-6,7-dihydro-1-oxo-1H,5H-benzo[ij]quinolizine-2-carboxylic acid was prepared from 9-fluoro-8-bromo-5-methyl-6,7-dihydro-1-oxo-1H,5H-benzo[ij]quinoline-2-carboxylic acid and morpholine. m.p. 279°–280° C., pale yellow rhombic crystals (DMF).

PREPARATION EXAMPLE 1

| | |
|---|---|
| Sodium 9-fluoro-8-(4-hydroxy-1-piperidyl)-5-methyl-6,7-dihydro-1-oxo-1H,5H—benzo[ij]quinolizine-2-carboxylate | 200 mg |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

PREPARATION EXAMPLE 2

| | |
|---|---|
| Sodium 9-fluoro-8-(4-hydroxy-1-piperidyl)-5-methyl-6,7-dihydro-1-oxo-1H,5H—benzo[ij]quinolizine-2-carboxylate | 100 g |
| Avicel (trade name for a product of Asahi Kasei Kogyo Kabushiki Kaisha) | 40 g |
| Corn Starch | 30 g |
| Magnesium Stearate | 2 g |
| TC-5 (trade name for hydroxypropyl-methyl cellulose, produced by Shinetsu Chemical Industry Co., Ltd) | 10 g |
| Polyethylene Glycol-6000 (molecular weight: 6,000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 3

| | |
|---|---|
| Sodium 9-fluoro-8-(4-hydroxy-1-piperidyl)-5-methyl-6,7-dihydro-1-oxo-1H,5H—benzo[ij]quinolizine-2-carboxylate | 2 g |
| Purified Hydrous Lanolin | 5 g |
| Japan Wax | 5 g |
| White Petrolatum | 88 g |

The Japan wax was heated until it was molten, and the active compound, purified hydrous lanolin, and white petrolatum were added thereto, followed by heat-melting. The mixture was stirred until it began to solidify to prepare an ointment.

PREPARATION EXAMPLE 4

| | |
|---|---|
| Sodium 9-fluoro-8-(morpholino-5-methyl-1-oxo-1H,5H—benzo[ij]-quinolizine-2-carboxylate | 100 g |
| Avicel (trade name for a product of Asahi Kasei Kogyo Kabushiki Kaisha) | 40 g |
| Corn Starch | 30 g |
| Magnesium Stearate | 2 g |
| TC-5 (trade name for hydroxypropyl-methyl cellulose, produced by Shinetsu Chemical Industry Co., Ltd.) | 10 g |
| Polyethylene Glycol-6000 (molecular weight: 6,000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 5

| | |
|---|---|
| Sodium 9-fluoro-(3,5-dimethyl-1-piperazinyl)-5-methyl-6,7-dihydro-1-oxo-1H,5H—benzo[ij]quinolizine-2-carboxylate | 100 g |
| Avicel (trade name for a product of Asahi Kasei Kogyo Kabushiki Kaisha) | 40 g |
| Corn Starch | 30 g |
| Magnesium Stearate | 2 g |
| TC-5 (trade name for hydroxypropyl-methyl cellulose, produced by Shinetsu Chemical Industry Co., Ltd.) | 10 g |
| Polyethylene Glycol-6000 (molecular weight: 6,000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 6

| | |
|---|---|
| 9-(1-Pyrrolidinyl)-8-fluoro-2-methyl-1,2-dihydro-6-oxo-pyrrolo[3,2,1-ij]-quinoline-5-carboxylic acid | 200 mg |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

PREPARATION EXAMPLE 7

| | |
|---|---|
| 9-Morpholino-8-fluoro-2-methyl-1,2-dihydro-6-oxo-pyrrolo[3,2,1-ij]-quinoline-5-carboxylic acid | 100 g |
| Avicel (trade name for a product of Asahi Kasei Kogyo Kabushiki Kaisha) | 40 g |
| Corn Starch | 30 g |
| Magnesium Stearate | 2 g |
| TC-5 (trade name for hydroxypropyl-methyl cellulose, produced by Shinetsu Chemical Industry Co., Ltd.) | 10 g |
| Polyethylene Glycol-6000 (molecular weight: 6,000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 8

| | |
|---|---|
| 9-(4-Trifluoromethyl-1-piperazinyl-8-fluoro-2-methyl-1,2-dihydro-6-oxo-pyrrolo[3,2,1-ij]-quinoline-5-carboxylic acid hydrochloride | 2 g |
| Purified Hydrous Lanolin | 5 g |
| Japan Wax | 5 g |
| White Petrolatum | 88 g |
| Total: | 100 g |

The Japan wax was heated until molten, and the active compound, purified hydrous lanolin and white petrolatum were added thereto followed by heat-melting. The mixture was stirred until it began to solidify to prepare an ointment.

PREPARATION EXAMPLE 9

| | |
|---|---|
| 9-(4-Trifluoromethyl-1-piperazinyl-8-fluoro-2-methyl-1,2-dihydro-6-oxo-pyrrolo[3,2,1-ij]quinoline-5-carboxylic acid hydrochloride | 200 mg |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

PREPARATION EXAMPLE 10

| | |
|---|---|
| Sodium 9-Fluoro-8-(morpholino-5-methyl-1-oxo-1H,5H—benzo[ij]-quinolizine-2-carboxylate | 200 mg |

| | |
|---|---|
| —continued | |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

While the invention has been described in detail and with reference to specific embodiments thereof, it will be apparent to one skilled in the art that various changes and modifications can be made therein without departing from the spirit and scope thereof.

What is claimed is:

1. A benzoheterocyclic compound of the formula (I)

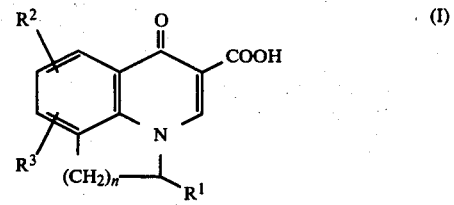

wherein $R^1$ represents a hydrogen atom or a lower alkyl group; $R^2$ represents a hydrogen atom or a halogen atom; $R^3$ represents a 1-pyrrolidinyl group which may be substituted with a hydroxymethyl group, a 1,2,5,6-tetrahydro-1-pyridyl group, or a group of the formula

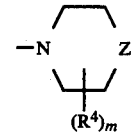

where $R^4$ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group, or a carbamoyl group; Z represents an oxygen atom, a sulfur atom or a methylene group; and m is 1 or 2; and n is an integer of 1 or 2; or its pharmaceutically acceptable salt.

2. A compound as claimed in claim 1, wherein n is 2.

3. A compound as claimed in claim 1, wherein n is 1.

4. A compound as claimed in claim 2, wherein $R^3$ represents a group of the formula

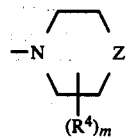

wherein Z, R and m have the same meanings as defined in claim 2.

5. A compound as claimed in claim 2, wherein $R^3$ represents a 1-pyrrolidinyl group which may be substituted with a hydroxymethyl group or a 1,2,5,6-tetrahydro-1-pyridyl group.

6. A compound as claimed in claim 4, wherein R⁴ represents a hydrogen atom, a hydroxy group or a lower alkanoyloxy group and the position at which the group of the formula

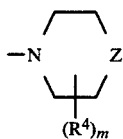

wherein Z, R⁴ and m have the same meanings as defined in claim 4, is attached is the 8-position.

7. A compound as claimed in claim 4, wherein R⁴ represents a lower alkyl group, a lower alkoxy group, a phenyl-lower alkyl group, an amino group which may be substituted with a lower alkyl group or a lower alkanoyl group, an oxo group, a carbamoyl group, and the position at which the group of the formula

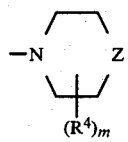

wherein Z, R⁴ and m have the same meanings as defined in claim 4, is attached is the 8-position.

8. A compound as claimed in claim 6, wherein R² represents a halogen atom.

9. A compound as claimed in claim 6, wherein R² represents a hydrogen atom.

10. A compound as claimed in claim 8, wherein R² represents a fluorine atom and the position at which the fluorine atom is attached is the 9-position.

11. A compound as claimed in claim 8, wherein R² represents a chlorine atom and the position at which the chlorine atom is attached is the 9-position.

12. A compound as claimed in claim 10, wherein R¹ represents a lower alkyl group.

13. A compound as claimed in claim 12, wherein R¹ represents a methyl group.

14. A compound as claimed in claim 11, wherein R¹ represents a methyl group.

15. A compound as claimed in claim 7, wherein R² represents a fluorine atom attached to the 9-position and R¹ represents a methyl group.

16. A compound as claimed in claim 5, wherein R¹ represents a methyl group, R² represents a fluorine atom attached to the 9-position and the position at which the group represented by R³ is attached is the 8-position.

17. A compound as claimed in claim 3, wherein the position at which R³ is attached is the 9-position.

18. A compound as claimed in claim 17, wherein R¹ represents a methyl group and R² represents a fluorine atom attached to the 8-position.

19. A compound as claimed in claim 17, wherein R¹ represents a methyl group and R² represents a chlorine atom attached to the 8-position.

20. 9-Fluoro-8-(4-hydroxy-1-piperidyl)-5-methyl-6,7-dihydro-1-oxo-1H,5H-benzo[ij]quinolizine-2-carboxylic acid as claimed in claim 1.

21. 9-Fluoro-8-(4-acetoxy-1-piperidyl)-5-methyl-6,7-dihydro-1-oxo-1H,5H-benzo[ij]quinolizine-2-carboxylic acid as claimed in claim 1.

22. 9-Fluoro-8-morpholino-5-methyl-6,7-dihydro-1-oxo-1H,5H-benzo[ij]quinolizine-2-carboxylic acid as claimed in claim 1.

23. An antibacterial composition comprising an antibacterially effective amount of a benzoheterocyclic compound of the formula (I)

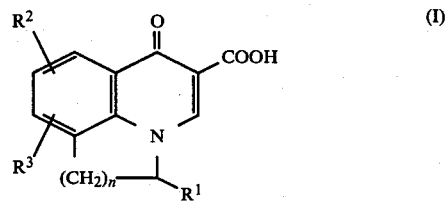

wherein R¹ represents a hydrogen atom or a lower alkyl group; R² represents a hydrogen atom or a halogen atom; R³ represents a 1-pyrrolidinyl group which may be substituted with a hydroxymethyl group, a 1,2,5,6-tetrahydro-1-pyridyl group, or a group of the formula

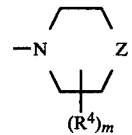

where R⁴ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group, or a carbamoyl group; Z represents an oxygen atom, a sulfur atom or a methylene group; and m is 1 or 2; and n is an integer of 1 or 2; or its pharmaceutically acceptable salt, as an active ingredient and a pharmaceutically acceptable carrier.

* * * * *